United States Patent
Allgeier et al.

(10) Patent No.: US 8,741,911 B2
(45) Date of Patent: Jun. 3, 2014

(54) RAF INHIBITOR COMPOUNDS

(71) Applicants: Eli Lilly and Company, Indianapolis, IN (US); Deciphera Pharmaceuticals, LLC, Lawrence, KS (US)

(72) Inventors: Matthew Carl Allgeier, Fishers, IN (US); Daniel L. Flynn, Lawrence, KS (US); Michael D. Kaufman, Lawrence, KS (US); Phenil J. Patel, Carmel, IN (US); Craig D. Wolfangel, Carmel, IN (US)

(73) Assignees: Eli Lilly and Company, Indianapolis, IN (US); Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 13/785,575

(22) Filed: Mar. 5, 2013

(65) Prior Publication Data

US 2013/0252977 A1     Sep. 26, 2013

Related U.S. Application Data

(60) Provisional application No. 61/607,702, filed on Mar. 7, 2012.

(51) Int. Cl.
*A01N 43/90* (2006.01)
*A61K 31/519* (2006.01)
*C07D 471/00* (2006.01)

(52) U.S. Cl.
USPC .................................. 514/264.11; 544/279

(58) Field of Classification Search
None
See application file for complete search history.

(56) References Cited

FOREIGN PATENT DOCUMENTS

| WO | 2006/039718 A2 | 4/2006 |
|---|---|---|
| WO | 2008/033999 A2 | 3/2008 |
| WO | 2008/034008 A2 | 3/2008 |
| WO | WO 2011/100319 A1 | 8/2011 |

OTHER PUBLICATIONS

Palmer B D, et al., "Structure-activity relationships for 2-anilino-6-phenylpyrido[2,3-d]pyrimidin-7(8H)—ones as inhibitors of the cellular checkpoint kinase Wee1," Bioorganic & Medicinal Chemistry Letters, 15(7):1931-1935 (2005).

*Primary Examiner* — Jeffrey H Murray
(74) *Attorney, Agent, or Firm* — Danica Hostettler; John Demeter

(57) ABSTRACT

The present invention provides a pyrido[2,3-d]pyrimidine compound, or a pharmaceutically acceptable salt thereof, that inhibits Raf and, therefore, may be useful in treating cancer.

22 Claims, 1 Drawing Sheet

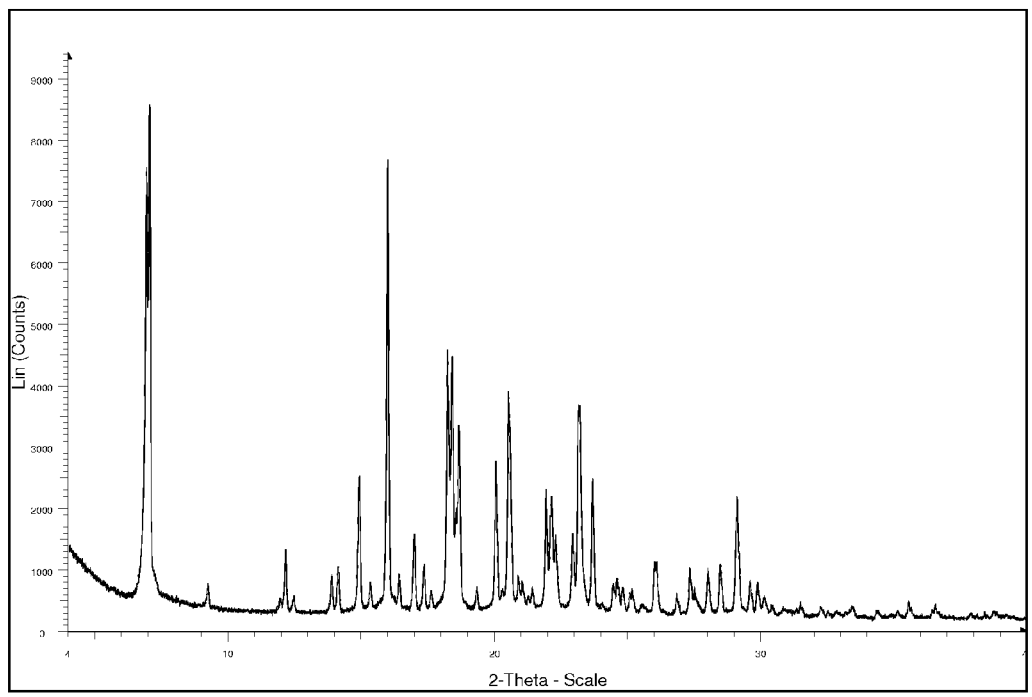

RAF INHIBITOR COMPOUNDS

The Ras/Raf/mitogen-activated protein kinase kinase (also known as MAP2K; MAPK kinase; and MAPK/ERK kinase or MEK)/extracellular signal-regulated kinase (ERK) signaling cascade (referred to herein as "Ras/Raf/MEK/ERK" or "Ras/Raf/MEK/MAPK") is an evolutionary conserved pathway that plays an integral role in development and tissue homeostasis in mammals. This signaling pathway consists of a kinase cascade that relays extracellular signals to the nucleus to regulate gene expression and key cellular functions. Gene expression controlled by the Ras/Raf/MEK/ERK signaling pathway regulates fundamental cellular processes including proliferation, differentiation, apoptosis, and angiogenesis. These diverse roles of Ras/Raf/MEK/ERK signaling are aberrantly activated in various types of cancer. Mutations in genes within this pathway may lead to constitutively active proteins resulting in increased cell proliferation, and resistance to apoptosis.

Raf (a serine/threonine-protein kinase) is encoded by a gene family consisting of three genes affording three Raf isoform members (B-Raf, C-Raf (Raf-1) and A-Raf). Each of these proteins share highly conserved amino-terminal regulatory regions and catalytic domains at the carboxy terminus. Unless otherwise indicated, Raf refers to all three members. Although each isoform plays a role in the Ras/Raf/MEK/ERK pathway, B-Raf has been shown to be the main activator of MEK. B-Raf is recruited by Ras:GTP to the intracellular cell membrane where B-Raf becomes activated. In turn, B-Raf is responsible for activation of MEK1/2 and MEK1/2 activate ERK1/ERK2. Mutations in the B-Raf gene allow for B-Raf to signal independently of upstream signals. As a result, mutated B-Raf protein (such as V600E) causes excessive downstream signaling of MEK and ERK. This leads to excessive cell proliferation and survival and oncogenesis. Overactivation of the signaling cascade by mutated B-Raf has been implicated in multiple malignancies.

The receptor tyrosine kinase (RTK) c-Kit (also called CD117), is expressed on a wide variety of cell types. The ligand for c-KIT is stem cell factor (SCF). The binding of SCF to the extracellular domain of c-KIT induces receptor dimerization and activation of downstream signaling pathways, including the RAS/RAF/MEK/ERK pathway. Mutant c-KIT has been implicated in the pathogenesis of several cancers.

Despite B-Raf specific inhibitors (such as vemurafenib), and compounds such as those disclosed in WO 2006/039718 and WO 2008/034008, there is a need for a Raf inhibitor active in inhibiting all isoforms of Raf proteins including A-Raf, B-Raf, C-Raf, and B-Raf V600E mutation. There is a further need for a Raf inhibitor that is active against tumor cells with upstream pathway activation by N-Ras mutations, K-Ras mutations, and cKit mutations. Furthermore, there remains a need to provide alternative Raf inhibitors for treatment of cancer. There also remains a need to provide alternative Raf inhibitors active in inhibiting A-Raf, B-Raf, C-Raf, and B-Raf V600E mutation for treatment of cancer. Accordingly, the present invention provides a Raf inhibitor which may be active in inhibiting all isoforms of Raf proteins. Also, the present invention provides a Raf inhibitor which may be active against tumor cells with upstream pathway activation by N-Ras mutations, K-Ras mutations, and cKit mutations. Additionally, the present invention provides an alternative inhibitor of Raf. Furthermore, the present invention provides an alternative inhibitor of Raf which may be useful for treating cancer. The present invention also provides an alternative inhibitor of Raf active in inhibiting A-Raf, B-Raf, C-Raf, and B-Raf V600E mutation. Still further, the present invention provides an alternative inhibitor of Raf active in inhibiting A-Raf, B-Raf, C-Raf, and B-Raf V600E mutation which may be useful for treating cancer.

FIG. 1 is a representative X-ray powder diffraction pattern for Example 1.

The present invention provides a compound which is 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof.

As a particular embodiment, the present invention provides the compound which is 1-(3,3-dimethylbutyl)-3-(2-fluoro-4-methyl-5-(7-methyl-2-(methylamino)pyrido[2,3-d]pyrimidin-6-yl)phenyl)urea.

The present invention provides a pharmaceutical composition comprising 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, in association with a pharmaceutically acceptable carrier. The present invention provides a pharmaceutical composition comprising 1-(3,3-dimethylbutyl)-3-(2-fluoro-4-methyl-5-(7-methyl-2-(methylamino)pyrido[2,3-d]pyrimidin-6-yl)phenyl)urea, in association with a pharmaceutically acceptable carrier.

The present invention provides a pharmaceutical composition comprising 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, and a pharmaceutically acceptable carrier, diluent, or excipient. The present invention provides a pharmaceutical composition comprising 1-(3,3-dimethylbutyl)-3-(2-fluoro-4-methyl-5-(7-methyl-2-(methylamino)pyrido[2,3-d]pyrimidin-6-yl)phenyl)urea, and a pharmaceutically acceptable carrier, diluent, or excipient.

As a particular embodiment, the present invention provides a pharmaceutical composition comprising 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, and polyvinyl pyrrolidone vinyl acetate (PVP-VA). The present invention also provides a pharmaceutical composition comprising 1-(3,3-dimethylbutyl)-3-(2-fluoro-4-methyl-5-(7-methyl-2-(methylamino)pyrido[2,3-d]pyrimidin-6-yl)phenyl)urea, and polyvinyl pyrrolidone vinyl acetate (PVP-VA). Furthermore, the present invention provides preferred embodiments of the pharmaceutical compositions as described herein, in which PVP-VA is selected from the group consisting of Kollidon® VA 64 and Plasdone™ S-630 copovidone. Preferably, the PVP-VA is Kollidon® VA 64.

A currently preferred formulation comprises 1-(3,3-dimethylbutyl)-3-{2-fluoro-4-methyl-5-[7-methyl-2-(methylamino)pyrido[2,3-d]pyrimidin-6-yl]phenyl}urea, or a pharmaceutically acceptable salt thereof, together with Kollidon® VA 64 (BASF Corporation Product No. 95405-2-43), a copolymer of 1-vinyl-2-pyrrolidone and vinyl acetate in a 60:40 ratio and 1-2% (w/w) sodium lauryl sulfate. A solid dispersion is prepared which may comprise a 20% or 40% drug load and may include 0-2% sodium lauryl sulfate or appropriate amount of other suitable pharmaceutically acceptable wetting agent, a plasticizer, processing aid or other suitable excipient(s).

The present invention provides a method for treating cancer comprising administering to a patient in need thereof an effective amount of 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof. The present invention provides a method for treating cancer comprising administering to a patient in need thereof an effective amount of 1-(3,3-dimethylbutyl)-3-(2-fluoro-4-methyl-5-(7-methyl-2-(methylamino)pyrido[2,3-d]pyrimidin-6-yl)phenyl)urea.

The present invention provides 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, for use in therapy. The present invention provides 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, for use in the treatment of cancer. The present invention provides a pharmaceutical composition for use in treating cancer, the pharmaceutical composition comprising 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof.

The present invention provides 1-(3,3-dimethylbutyl)-3-(2-fluoro-4-methyl-5-(7-methyl-2-(methylamino)pyrido[2,3-d]pyrimidin-6-yl)phenyl)urea for use in therapy. The present invention provides 1-(3,3-dimethylbutyl)-3-(2-fluoro-4-methyl-5-(7-methyl-2-(methylamino)pyrido[2,3-d]pyrimidin-6-yl)phenyl)urea for use in the treatment of cancer. The present invention provides a pharmaceutical composition for use in treating cancer, the pharmaceutical composition comprising 1-(3,3-dimethylbutyl)-3-(2-fluoro-4-methyl-5-(7-methyl-2-(methylamino)pyrido[2,3-d]pyrimidin-6-yl)phenyl)urea.

The present invention provides the use of 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, in the manufacture of a medicament for the treatment of cancer. The present invention also provides the use of 1-(3,3-dimethylbutyl)-3-(2-fluoro-4-methyl-5-(7-methyl-2-(methylamino)pyrido[2,3-d]pyrimidin-6-yl)phenyl)urea in the manufacture of a medicament for the treatment of cancer.

The present invention provides 1-(3,3-dimethylbutyl)-3-(2-fluoro-4-methyl-5-(7-methyl-2-(methylamino)pyrido[2,3-d]pyrimidin-6-yl)phenyl)urea in crystalline form. The present invention also provides 1-(3,3-dimethylbutyl)-3-(2-fluoro-4-methyl-5-(7-methyl-2-(methylamino)pyrido[2,3-d]pyrimidin-6-yl)phenyl)urea in crystalline form characterized by a X-ray powder diffraction pattern having characteristic peaks, in 2θ±0.2, occurring at 16.0 and one or more of 6.9, 7.0, 18.2, and 23.2.

Furthermore, the present invention provides preferred embodiments of the methods and uses as described herein, in which cancer is selected from the group consisting of acute myelogenous leukemia (AML, acute myeloid leukemia), chronic myelogenous leukemia (CML), chronic lymphoblastic leukemia (CLL), myelodysplastic syndrome, ovarian cancer, melanoma, small-cell lung cancer, non-small-cell lung cancer, colorectal cancer, pancreatic cancer, prostate cancer, liver cancer or thyroid cancer. More preferably, the cancer is selected from the group consisting of thyroid cancer, ovarian cancer, melanoma, acute myelogenous leukemia (AML, acute myeloid leukemia), and colorectal cancer. Even more preferably, the cancer is melanoma or colorectal cancer.

A method of treating a cancer which is thyroid cancer, ovarian cancer, melanoma, AML or colorectal cancer in a patient comprising administering to a patient in need thereof a therapeutically effective amount of 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof.

A compound which is 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, for use in therapy.

A compound which is 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, for use in the treatment of a cancer which is thyroid cancer, ovarian cancer, melanoma, AML or colorectal cancer.

Use of 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, for the manufacture of a medicament for the treatment of a cancer which is thyroid cancer, ovarian cancer, melanoma, AML or colorectal cancer.

In a particular embodiment, the pharmaceutical composition comprises, 1-(3,3-dimethylbutyl)-3-{2-fluoro-4-methyl-5-[7-methyl-2-(methylamino)pyrido[2,3-d]pyrimidin-6-yl]phenyl}urea, or a pharmaceutically acceptable salt thereof, together with a pharmaceutically acceptable carrier and optionally other therapeutic ingredients.

In a particular embodiment, the pharmaceutical composition comprises 1-(3,3-dimethylbutyl)-3-{2-fluoro-4-methyl-5-[7-methyl-2-(methylamino)pyrido[2,3-d]pyrimidin-6-yl]phenyl}urea, or a pharmaceutically acceptable salt thereof, together with a pharmaceutically acceptable carrier and optionally other therapeutic ingredients particularly for treatment of cancer generally or a specific cancer type.

The present invention provides a compound of the formula:

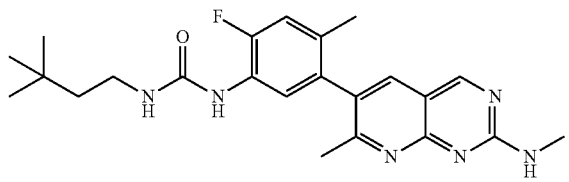 [SMILES: CNc1ncc2cc(-c3cc(NC(=O)NCCC(C)(C)C)c(F)cc3C)c(C)nc2n1]

or a pharmaceutically acceptable salt thereof.

The term "patient" means mammal and "mammal" includes, but is not limited to, a human.

"Therapeutically effective amount" or "effective amount" means the dosage of the compound, or pharmaceutically acceptable salt thereof, or pharmaceutical composition containing the exemplified compound, or pharmaceutically acceptable salt thereof, necessary to inhibit B-Raf, C-Raf, A-Raf and/or B-Raf V600E signaling in a cancer patient, and either destroy the target cancer cells or slow or arrest the progression of the cancer in a patient. Anticipated dosages of the exemplified compound, or a pharmaceutically acceptable salt thereof, are in the range of 300 to 1500 mg/patient/day. Preferred dosages are anticipated to be in the range of 400 to 1400 mg/patient/day. Most preferred dosages are anticipated to be in the range of 600 to 1200 mg/patient/day. The exact dosage required to treat a patient and the length of treatment time will be determined by a physician in view of the stage and severity of the disease as well as the specific needs and response of the individual patient and the particular compound administered. Although expressed as dosage on a per day basis, the dosing regimen may be adjusted to provide a more optimal therapeutic benefit to a patient. In addition to daily dosing, twice-a-day (BID) or thrice-a-day (TID) dosing may be appropriate. BID dosing is currently preferred.

The terms "treatment," "treat," and "treating," are meant to include the full spectrum of intervention for the cancer from which the patient is suffering, such as administration of the active compound to alleviate, slow or reverse one or more of the symptoms of the cancer and to delay progression of the cancer even if the cancer is not actually eliminated.

The exemplified compound of the present invention is preferably formulated as a pharmaceutical composition using a pharmaceutically acceptable carrier or using one or more pharmaceutically acceptable carriers, diluents, or excipients and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 21$^{st}$ ed., Mack Publishing Co., 2005).

The exemplified compound of the present invention is capable of reaction with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

It should be understood that 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, may be prepared by a variety of procedures known in the art, as well as those described below.

Example 1 is named: 1-(3,3-dimethylbutyl)-3-{2-fluoro-4-methyl-5-[7-methyl-2-(methylamino)pyrido[2,3-d]pyrimidin-6-yl]phenyl}urea; and may also be named: N-(3,3-dimethylbutyl)-N'-{2-fluoro-4-methyl-5-[7-methyl-2-(methylamino)pyrido[2,3d]pyrimidin-6-yl]phenyl}urea; and other names may be used to unambiguously identify Example 1.

The compounds employed as initial starting materials in the synthesis of 1-(3,3-dimethylbutyl)-3-(2-fluoro-4-methyl-5-(7-methyl-2-(methylamino)pyrido[2,3-d]pyrimidin-6-yl)phenyl)urea are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

As used herein, the following terms have the meanings indicated: "d6-DMSO" refers to hexadeutero-dimethylsulfoxide; "DCM" refers to dichloromethane; "DMSO" refers to dimethylsulfoxide; "EtOAc" refers to ethyl acetate; "EtOH" refers to ethanol; "HPLC" refers to high performance liquid chromatography; "IPAC" refers to isopropyl acetate; "KF" refers to Karl Fischer; "MS" refers to mass spectroscopy; "MeOH" refers to methanol; "MTBE" refers to tert-butyl methyl ether; "NMR" refers to nuclear magnetic resonance; "RT" refers to room temperature; "THF" refers to tetrahydrofuran.

Unless noted to the contrary, the compounds illustrated herein are named and numbered using either ACDLABS or Symyx Draw 3.2.

PREPARATION 1

5-Bromo-2-fluoro-4-methylaniline

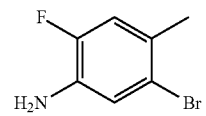

Method A:

Combine 1-bromo-4-fluoro-2-methylbenzene (30.0 g, 159 mmol) in concentrated sulfuric acid (100 mL), cool to about −5° C., and treat dropwise with nitric acid (11.00 mL, 174 mmol) over 20 minutes. Allow reaction mixture to warm to RT and stir for 30 min. Pour onto crushed ice with stirring and partition with tert-butyl methyl ether (MTBE) (200 mL). Separate the aqueous layer and extract with MTBE (2×50 mL). Combine organic layers, dry and concentrate under reduced pressure to provide 1-bromo-4-fluoro-2-methyl-5-nitrobenzene as an orange-colored viscous oil (39.0 g).

Combine crude 1-bromo-4-fluoro-2-methyl-5-nitrobenzene (32.4 g, 138 mmol), ethanol (100 mL) and Raney Nickel (1.00 g, 17.04 mmol) in a shaker flask. Charge the flask with hydrogen (275 kPa) and agitate until the absorption of hydrogen ceases. De-pressurize the reaction vessel, remove the catalyst by filtration, and evaporate the filtrate to dryness. Add MTBE, then filter again and evaporate the filtrate. Stir residue in hexanes. Collect the solids by filtration, wash with cold hexanes and dry in vacuo to provide the title compound (17.8 g, 63% yield) as a dark solid. MS (m/z): 204.0 (M+1)/206.0 (M+3).

Method B:

To a 4 necked round bottom flask equipped with mechanical agitation, thermometer, ice bath and N$_2$ inlet is added 1-bromo-4-fluoro-2-methylbenzene (1.4 kg, 7.4 mol), then concentrated H$_2$SO$_4$ (6.3 kg) is added at 0-10° C. After stirring for 10-20 minutes, the mixture is cooled to −10~0° C., and KNO$_3$ (0.82 kg, 7.8 mol, 1.05 equiv.) is added in portions in about 6 hours while maintaining the temperature at −10~0° C. After the addition, the reaction mixture is warmed to 10-20° C., and monitored by TLC (EA:PE=1:20) and HPLC until the content of 1-bromo-4-fluoro-2-methylbenzene is <0.5%. The mixture is poured into ice/water mixture (11.2 kg, Ice:water=1:1) and extracted twice with MTBE (4.7 L and 1.9 L). The organic layers are combined, washed with saturated brine (5.6 kg) and concentrated to 1.5~2V below 45° C. under reduce pressure. The residue is diluted with EtOAc (5.6 L) and the resulting solution is used directly into the next step (1.22 kg (wt % corrected), 70.5% yield, and 68.3% purity detected by UV absorption at 210 nm). $^1$H NMR (400 MHz, CDCl$_3$): δ 8.35 (s, J=7.1 Hz, 1H), 7.29 (d, J=11.3 Hz, 1H), 2.59 (d, J=6.8 Hz, 3H).

To a 4 necked round bottom flask equipped with mechanical agitation, thermometer and N$_2$ inlet is added a solution of 1-bromo-4-fluoro-2-methyl-5-nitrobenzene (1.16 kg, 4.96 mol.) in EtOAc (5 L) and 36% HCl solution (4.9 kg, 49.6 mol, 10.0 equiv.). After stirring for 5~10 minutes at 20~30° C., Fe powder (1.34 kg, 24.0 mol, 4.8 equiv.) is added in portions while maintaining the temperature at 20-30° C. The reaction is monitored by TLC (EA:PE=1:10). After the completion of the reaction, the pH value is adjusted to 2~3 using NaHCO$_3$, and Celite® (0.56 kg) is added. The mixture is stirred for 0.5~1 hour and filtered. The solid is washed with toluene (2×2.6 L). The filtrates are combined and stirred for another 0.5~1 h before separation of the layers. The aqueous layer is extracted with toluene (2.6 L). The organic layers are combined, washed with brine (3 L), and filtered through a silica gel pad (2~3 cm). The filtrate is concentrated to 2~2.5 L and the residue is mixed with n-Heptane (3.3 L). After concentrated to 2~2.5 L again, n-heptane (1.65 L) is added. The mixture is cooled to −10~−0° C. and stirred for 1 hour. The precipitate is collected by filtration, washed with n-heptane (0.5 L, pre-cooled to −10~0° C.), and dried to afford the crude product of the title compound as a brown solid. Recrystallization of crude product with n-Heptane (3.3 L) gives off-white to brown solid of title compound. (527 g, 52% yield and 98% purity detected by UV absorption at 210 nm). $^1$H NMR (400 MHz, d6-DMSO): δ 6.97 (m, 2H), 5.18 (s, 2H), 2.16 (s, 3H); $^{13}$C NMR (500 MHz, CDCl$_3$): δ 21.41, 116.60, 118.30, 119.66, 127.22, 132.88, (149.37, 151.12); $^{19}$F NMR (400 MHz, CDCl$_3$): δ 151.14

PREPARATION 2

2-Fluoro-4-methyl-5-(4,4,5,5-tetramethyl-1,3,2-dioxaborolan-2-yl)aniline

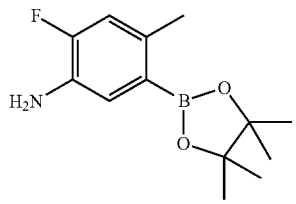 [SMILES: Cc1cc(F)c(N)cc1B1OC(C)(C)C(C)(C)O1]

Method A:

Combine 5-bromo-2-fluoro-4-methylaniline (3.1 g, 15.2 mmol), bis(pinacolato)diboron (4.24 g, 16.7 mmol), and potassium acetate (4.47 g, 45.6 mmol) in dioxane (40 mL) and sparge with argon. Add [1,1'-bis(diphenylphosphino)ferrocene]-dichloropalladium(II)-dichloromethane complex (0.620 g, 0.760 mmol), sparge again with argon and heat at 100° C. overnight. Filter the reaction mixture and concentrate in vacuo. Purify by silica gel chromatography (0-50% EtOAc/hexanes) to give the title compound (3.24 g, 85% yield). MS (m/z): 252.1 (M+1).

Method B:

To 4 necked round bottom flask. equipped with mechanical agitation, thermometer, and N$_2$ inlet is added 5-bromo-2-fluoro-4-methylaniline (200 g, 0.98 mol), CH$_3$COOK (192 g, 1.95 mol, 2.0 eq), bis(pinacolato)diboron (248 g, 0.98 mol, 1.0 eq) and IPAC (3 L). After degassing with N$_2$ for 30 min, the mixture is warmed to 50° C. and Pd(dppf)Cl$_2$ (8 g, 4 wt %) is added. The reaction mixture is heated under reflux for at least 10 h until the content of starting material ≤2% (GC). The mixture is cooled to 20~30° C., filtered through a pad of Celite® and rinsed with IPAC (1 L). The filtrate is concentrated to 400~500 ml remaining. The residue is mixed with n-Heptane (700 ml), filtered through a SiO$_2$ pad and eluted with IPAC/n-Heptane (1/5 first, ~2 L, and then 2/5, ~3 L). The filtrate is concentrated to 350~400 ml. n-Heptane (300 ml) is added and the mixture is again concentrated to 350~400 ml. The residue (suspension) is cooled to −10~−20° C. and filtered after stiffing for 2-5 h. The crude product is dissolved in MeOH (200 ml) at 30~40° C., then slowly add H$_2$O (600 ml) dropwise in 0.5~1 h. The suspension is cooled to 20~30° C. and filtered after stirring for 1-2 h. The solid is dried under high vacuum to afford the title compound as off-white solid (183 g, 74% yield and 99% purity detected by UV absorption at 210 nm; $^1$H NMR (400 MHz, CDCl$_3$): δ 7.42 (d, J=10.2 Hz, 1H), 7.01 (d, J=12.4 Hz, 1H), 3.76 (s, 2H), 2.64 (s, 3H), 1.55 (s, 12H); $^{13}$C NMR (500 MHz, CDCl$_3$): δ 20.66, 20.67, 24.40, 82.93, 116.20, 124.37, 130.64, 135.02, (151.93, 153.37); $^{19}$F NMR (400 MHz, CDCl$_3$): δ 145.72

PREPARATION 3

Prop-1-en-2-yl 2-fluoro-4-methyl-5-(4,4,5,5-tetramethyl-1,3,2-dioxaborolan-2-yl)phenylcarbamate

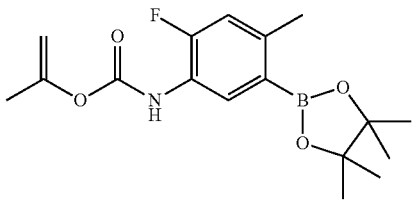 [SMILES: C=C(C)OC(=O)Nc1cc(B2OC(C)(C)C(C)(C)O2)c(C)cc1F]

Add 2-fluoro-4-methyl-5-(4,4,5,5-tetramethyl-1,3,2-dioxaborolan-2-yl)aniline (5.0 g, 19.91 mmol) and isopropenyl chloroformate (2.40 mL, 21.90 mmol) in EtOAc (60 mL) and saturated aqueous NaHCO$_3$ (60 mL) and stir at RT for 6 h. Separate the layers, extract the aqueous layer with EtOAc (2×), wash the combined organics with brine, dry over Na$_2$SO$_4$ and concentrate to obtain the title compound. Use for the next reaction without further purification (assuming 100% yield). MS (m/z): 336.2 (M+1).

PREPARATION 4

3,3-Dimethylbutan-1-amine hydrochloride

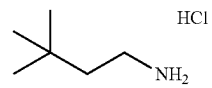

To 4 necked round bottom flask equipped with mechanical agitation, thermometer and N$_2$ inlet is added 3,3-dimethylbutanal (200 g, 2.0 mol). Then 1-phenylmethanamine (214 g, 2.0 mol, 1.0 equiv.) is added dropwise. The reaction mixture is stirred at 20~30° C. for 2~5 hour until greater than 99% conversion by GC. NaCl (4 g) is added and the aqueous phase is discarded. THF (800 ml) is added and the mixture is concentrated to 400 ml. This operation is repeated until the KF of the residue is less than 0.2%. THF (800 ml) and t-BuOK (44.8 g, 0.4 mol, 0.2 eq) is added. The mixture is warmed to 60~65° C. and stirred until the content of N-benzyl-3,3-dimethylbutan-1-imine is less than 1% by GC. After cooling to 10-20° C., water (1500 ml) is added and the mixture is extracted with MTBE (2×1500 ml). The combined organic phase is washed with saturated NaCl (800 ml), sampled for water content analysis and ensure 1%-2% KF content. The stream of N-(3,3-dimethylbutyl)-1-phenyl-methanimine is used directly for the next step. (83% purity by GC; GC-MS m/z 188.2 [M-H]+).

To 4 necked round bottom flask equipped with mechanical agitation, thermometer and N₂ inlet is added N-(3,3-dimethylbutyl)-1-phenyl-methanimine solution obtained above (412 g, 2.18 mol, 3.27 L MTBE 1.3 L THF.) and HCl/MTBE solution (16%, 398 g, 1.74 mol, 0.8 eq) is added dropwise at 20~30° C. White solid precipitated during the addition. After stiffing for 1~2 hrs, an aliquot sample of the suspension was filtered. The mother liquor is checked by GC. If the content of N-(3,3-dimethylbutyl)-1-phenyl-methanimine is greater than 30%, an additional HCl/MTBE solution (45 g, 0.10 eq) is added until the content of N-(3,3-dimethylbutyl)-1-phenyl-methanimine is between 20%~30% by GC. The solid is collected by filtration washed with MTBE (870 ml), and dried under N₂ to give the desired title compound as a white crystalline material (195 g, 65% yield; ¹H NMR (400 MHz, d6-DMSO): δ 7.90 (s, 3H), 2.74 (m, 2H), 1.47 (m, 2H), 0.89 (s, 9H); ¹³C NMR (500 MHz, d6-DMSO): δ 28.98, 29.31, 35.49, 40.34.

PREPARATION 5

1-(3,3-Dimethylbutyl)-3-(2-fluoro-4-methyl-5-(4,4,5,5-tetramethyl-1,3,2-dioxaborolan-2-yl)phenyl)urea

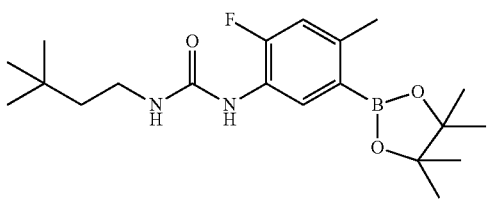 [SMILES: Cc1cc(F)c(NC(=O)NCCC(C)(C)C)cc1B1OC(C)(C)C(C)(C)O1]

Method A:

Treat a solution of prop-1-en-2-yl 2-fluoro-4-methyl-5-(4,4,5,5-tetramethyl-1,3,2-dioxaborolan-2-yl)phenylcarbamate (6.67 g, 19.90 mmol) in dioxane (60 mL) with 3,3-dimethylbutan-1-amine (2.42 g, 23.9 mmol) and 1-methylpyrrolidine (0.169 g, 1.99 mmol) and heat at 75° C. overnight. Cool the mixture to RT, collect the solid via filtration and wash with diethyl ether to obtain the title compound (6.62 g, 88% yield over two steps). MS (m/z): 379.2 (M+1).

Method B:

To 4 necked round bottom flask equipped with mechanical agitation, thermometer and N₂ inlet is added 2-fluoro-4-methyl-5-(4,4,5,5-tetramethyl-1,3,2-dioxaborolan-2-yl)aniline (40 g, 0.159 mol), THF (600 ml) and NaHCO₃ (16.0 g, 0.19 mol, 1.20 eq). The mixture is cooled to 0~5° C. and phenyl chloroformate (26.14 g, 0.167 mol, 1.05 eq) is added dropwise. The reaction mixture is warmed to 60° C. and stirred until the content of 2-fluoro-4-methyl-5-(4,4,5,5-tetramethyl-1,3,2-dioxaborolan-2-yl)aniline≤2%. The mixture is filtered and the solid (salt) is washed with THF (120 ml). The filtrate is concentrated to 65~80 ml. To the residue, toluene (720 ml), 3,3-dimethylbutan-1-amine (HCl salt, 26.14 g, 0.19 mol, 1.2 eq) and TEA (20.87 g, 0.21 mol, 1.3 eq) are added. The resulting mixture is heated to 90° C. and stirred until the content of intermediate ≤2%. The mixture is cooled to 15~20° C., stirred for 2 hrs and filtered. The solid is washed with toluene (120 ml), H₂O (2×400 ml) and dried under high vacuum to afford title compound as a white solid. (54.9 g, 91.3% yield and 99% purity detected by UV absorption at 210 nm); ¹H NMR (400 MHz, d6-DMSO): δ 8.34 (d, J=9.1 Hz, 1H), 8.08 (s, 1H), 6.98 (d, J=12.3 Hz, 1H), 6.41 (s, 1H), 3.08 (s, 2H), 2.38 (s, 3H), 1.36 (m, 14H), 0.90 (s, 9H); ¹³C NMR (500 MHz, d6-DMSO): δ 21.12, 24.65, 29.37, 29.58, 35.65, 43.50, 83.25, 104.32 116.09, 125.02, 128.19, 138.71, (152.40, 154.34), 154.81; ¹⁹F NMR (400 MHz, d6-DMSO): δ 136.34

PREPARATION 6

Ethyl 4-amino-2-(methylthio)pyrimidine-5-carboxylate

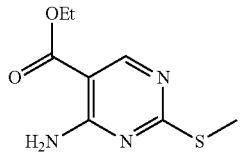

Method A:

Add concentrated ammonium hydroxide (335 mL, 8.60 mol) to a vigorously stirred suspension of ethyl 4-chloro-2-(methylthio)pyrimidine-5-carboxylate (200 g, 860 mmol) in ethanol (EtOH) (450 mL) and allow to stir overnight. Collect the solids by filtration, rinse with EtOH (2×100 mL) and H₂O (3×200 mL) and dry in a vacuum oven (65-70° C.) overnight to afford the title compound (164.4 g, 90% yield) as a white solid. MS (m/z): 214.1 (M+1).

Method B:

Charge reaction vessel with 1190 g of THF and 660 g of ethyl 4-chloro-2-(methylsulfanyl)pyrimidine-5-carboxylate (1.0 eq. 2.84 mol). Stir at 10~20° C. for 20-30 mins, and then add 907 g of NH₃—H₂O and 989 g of Et₃N to the mixture. Heat to 45-55° C., and stir for 2-6 hrs at 45-55° C. After reaction is complete, cool to 8-12° C. and add 4000 g water. Stir for 4-8 hrs at 8-12° C., filter and risen with 200 g water. Dry the cake in vacuum at 80° C. for 8-24 hrs to obtain title compound (560 g; 98.8% purity in 92% yield; [M+1]=213.8, ¹H NMR (d6-DMSO, 400 MHz): δ=8.564 (s, 1H), 8.278 (s, 1H), 8.011 (s, 1H), 7.649 (s, 1H), 4.293-4.240 (dd, J₁=6.8, J₂=14, 2H), 2.462 (s, 3H), δ 1.308-1.272 (m, 3H)).

PREPARATION 7

4-Amino-2-(methylthio)pyrimidin-5-yl)methanol

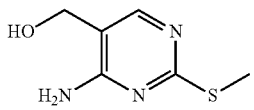

Cool a solution of ethyl 4-amino-2-(methylthio)pyrimidine-5-carboxylate (72.3 g, 339 mmol) in tetrahydrofuran (THF) (900 mL) to 0° C. Add a solution of LiAlH₄ (2 M in THF) (195 mL, 390 mmol) dropwise over 1 h. Stir for 2 h at 0° C. and allow the reaction to warm to RT overnight. Cool the mixture to 0° C. and cautiously quench by the sequential addition of water (15 mL), 20% aq. KOH (15 mL) and water (30 mL). Stir the resulting mixture for 1 h. Dry over MgSO₄, filter, concentrate under reduced pressure, and dry under vacuum to obtain the title compound (55.85 g, 96% yield). MS (m/z): 172.1 (M+1).

PREPARATION 8

4-amino-2-(methylthio)pyrimidine-5-carbaldehyde

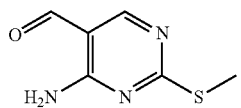

Method A:

Add MnO$_2$ (49.8 g, 572 mmol) to a suspension of 4-amino-2-(methylthio)pyrimidin-5-yl)methanol (28 g, 164 mmol) in chloroform (818 mL) and heat the reaction at 55° C. (measure internally) for 4 h. Filter the hot reaction mixture and rinse the filter cake with hot chloroform and THF. Concentrate the combined filtrates under reduced pressure and dry under vacuum to afford the title compound (26.7 g, 96% yield) as a pale yellow solid MS (m/z): 170.1 (M+1).

Method B:

Charge a reaction vessel with 450 g (2.08 mol, 1.0 eq.) of ethyl 4-amino-2-(methylthio)pyrimidine-5-carboxylate and 6750 mL (15.0 V) of THF. In a separate reaction vessel charge 88.1 g (1.1 eq.) of LiAlH$_4$ and 2250 g (5.0 V) of THF. Cool this LiAlH$_4$ mixture to −5~5° C. Add the THF solution of ethyl 4-amino-2-(methylthio)pyrimidine-5-carboxylate drop-wise to the LiAlH$_4$ mixture below 10° C. After addition, stir the mixture at 5~15° C. for 2~3 hours. Cool to −5~5° C. and add 279 g (1.5 eq.) of EtOAc drop-wise below 20° C. Stir the mixture at 10~20° C. for 1~2 hours. Add 450 g (0.66 eq.) of Na$_2$SO$_4$.10H$_2$O in portions below 20° C. Stir the mixture at 10~20° C. for 1~2 hours. Filter the suspension through diatomaceous earth. Wash the cake with THF. Charge 734 g (4.0 eq.) of MnO$_2$ to the filtrate containing 4-amino-2-(methylthio)pyrimidin-5-yl)methanol solution. Heat the mixture to 40° C. Stir the mixture at 40~45° C. for 6~8 hours. Filter the suspension through diatomaceous earth. Wash cake with THF. Combine the filtrate, concentrate and add 1530 g (5.0 V) of n-Heptane drop-wise. Stir the mixture at 10~20° C. for 3~4 hours. Filter the suspension and wash the cake with heptane. Dry the filter cake under reduced pressure at 40~50° C. for 10-16 hrs. to afford title compound (276 g; 97.9% purity in 75% yield; [M+1]=171.8, $^1$H NMR (d6-DMSO, 400 MHz): δ=7.887 (s, 1H), 6.704 (s, 2H), 5.066-5.042 (m, 1H), δ 4.292-4.280 (d, 2H), 2.392 (s, 3H); [M+1]=169.8, $^1$H NMR (CDCl$_3$, 400 MHz): δ=9.769 (s, 1H), 8.414 (s, 1H), 8.190 (s, 1H), 5.772 (s, 1H), 2.540 (s, 3H)).

PREPARATION 9

7-Methyl-2-(methylthio)pyrido[2,3-d]pyrimidin-6-ol

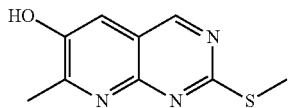

Method A:

Add 1-hydroxypropan-2-one (24.3 mL, 355 mmol) and 4-amino-2-(methylthio)pyrimidine-5-carbaldehyde (50 g, 296 mmol) to a solution of sodium hydroxide (23.64 g, 591 mmol) and water (200 mL). Add EtOH (600 mL) to the suspension and stir at RT overnight. Slowly add a solution of concentrated HCl (50 mL) in water (350 mL). Add 1:1 EtOH/H$_2$O (100 mL) and collect the solids by filtration. Wash the solids with 1:1 EtOH/H$_2$O (250 mL), ice cold EtOH (4×25 mL) and hexanes (2×250 mL). Dry in the vacuum oven at 30-35° C. to provide the title compound as a tan solid (34 g, 56% yield). MS (m/z): 208.1 (M+1).

Method B:

Charge reaction vessel with 2400 g (8.0 V) of H$_2$O and 177.3 g (2.5 eq.) of NaOH and 300.0 g (1.77 mol, 1.0 eq.) of 4-amino-2-(methylthio)pyrimidine-5-carbaldehyde and 157.6 g (1.2 eq.) of Hydroxyacetone. Heat the mixture to 35-45° C. and stir for 10-20 hrs at 35-45° C. Cool the mixture to 5-15° C. Add 4500 mL of 1N HCl drop-wise and adjust pH to 3~4 below 15° C. Stir for 1-2 hrs at 10-15° C. Filter and rinse cake with 300 g of water. Dry the filter cake under reduced pressure at 50~60° C. for 16-24 hrs. to provide title compound (372 g of brown solid; 98.0% HPLC area (assay: 90.0%); 90% yield; $^1$H NMR (d6-DMSO, 400 MHz): δ=10.864 (s, 1H), 9.276 (s, 1H), 7.529 (s, 1H), 2.570 (s, 6H)).

PREPARATION 10

7-Methyl-2-(methylthio)pyrido[2,3-d]pyrimidin-6-yl trifluoromethanesulfonate

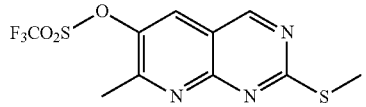

Method A:

Combine 7-methyl-2-(methylthio)pyrido[2,3-d]pyrimidin-6-ol (25 g, 121 mmol), DCM (1100 mL) and pyridine (98 mL, 1206 mmol) and cool the mixture with an ice bath until the internal temperature <3° C. Add trifluoromethanesulfonic anhydride (24.5 mL, 145 mmol) slowly via syringe at such a rate that the internal temperature is maintained below 5° C. Stir the reaction mixture at 0° C. for 2 h. Wash with water (3×300 mL) and brine (300 mL), dry over MgSO$_4$, and filter. Concentrate the filtrate under reduced pressure (water bath temp ~35° C.) and dry under high vacuum for 2-3 h at RT. Dissolve the residue in DCM and purify by silica gel chromatography (EtOAc/hexanes). Concentrate fractions to afford a semi-pure solid. Triturate the solid with 20% EtOAc/hexanes (100 mL), collect by filtration, rinse with 20% EtOAc/hexanes (2×10 mL) and dry under vacuum at RT to afford the title compound as a pale pink solid (28.6 g, 70% yield). MS (m/z): 340.0 (M+1).

Method B:

Charge reaction vessel with 4000 mL (20.0 V) of DCM and 208 g (1.0 mol, 1.0 eq.) of 7-methyl-2-(methylthio)pyrido[2,3-d]pyrimidin-6-ol. Stir the mixture for 10-20 mins. Charge 312 g (4.0 eq.) of Pyridine below 20° C. Cool to −5~0° C. and add the solution of 416 g of Trifluoromethanesulfonic anhydride (1.5 eq.) in DCM (2000 mL, 10.0 V) drop-wise below 0° C. After addition, stir at 0-5° C. for 2-3 hours. Quench reaction with 2000 mL of 1N HCl (2×). Wash with 500 mL of H$_2$O twice. Add 100.0 g of silica gel and stir at 10~20° C. for 1-2 hours. Filter the mixture through diatomaceous earth. Concentrate filtrate and add n-heptane 1000 mL (5.0 V) drop wise with stirring at 10~20° C. Stir the mixture at 10~20° C. for 3-4 hours. Filter and dry the cake under reduced pressure at 35~40° C. for 8-12 hrs. to afford title compound (307 g of brown solid; 99.1% HPLC area (assay: 96.8%); 86% yield; $^1$H NMR (CDCl$_3$, 400 MHz): δ=9.216 (s, 1H), 8.120 (s, 1H), 2.890 (s, 3H), 2.773 (s, 3H).

PREPARATION 11

7-Methyl-2-(methylamino)pyrido[2,3-d]pyrimidin-6-yl trifluoromethanesulfonate

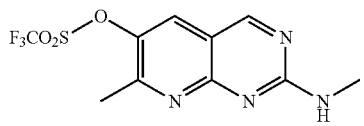

Method A:

Heat a mixture 7-methyl-2-(methylthio)pyrido[2,3-d]pyrimidin-6-yl trifluoromethanesulfonate (28.6 g, 84 mmol), dimethylformamide (74 mL) and glacial acetic acid (9.61 mL, 169 mmol) to 45° C. and then add 6.15% aqueous NaOCl (bleach, 612 g, 506 mmol) dropwise over 2 h. Heat at 45-50° C. for 2 h, cool to RT, collect the solids by filtration and wash with water (300 mL). Add DCM (200 mL) to the solids, cool the suspension in an ice-water bath and treat with a solution of 2.0 M N-methylamine in THF (126 mL, 253 mmol). Allow the mixture to slowly warm to RT and stir for 2 h. Remove the solvent under reduced pressure, treat with methanol (MeOH) (50 mL) and stir at RT for 30 min. Collect the solid by filtration and wash with MeOH. Treat the solid with EtOAc (30 mL) and stir at RT for 30 min. Collect the solid by filtration and wash with EtOAc to obtain the title compound (19.82 g, 73% yield). MS (m/z): 323.0 (M+1).

Method B:

Charge reaction vessel with 150 g (0.442 mol, 1.0 eq. Limited Reagent) of 7-methyl-2-(methylthio)pyrido[2,3-d]pyrimidin-6-yl trifluoromethanesulfonate, add 3000 mL DCM to clear, cool the mixture to −5~5° C. Add 105 g (0.442 mol, 1.0 eq.) of m-CPBA in portions below 5° C. Stir the mixture at 0~5° C. for 3~4 hours (E/A=1%). Add 660 mL (1.326 mol, 3.0 eq.) of Methylamine in 2M THF drop-wise below 10° C., stir the mixture at 0~10° C. for 3~4 hours. Add 1500 mL DCM and 1000 mL H$_2$O with stiffing and separate the aqueous layer. Wash the organic layer with 500 mL H$_2$O four times and concentrate to 600 g below 40° C. Solvent exchange with n-heptane twice and stir the mixture at 10~20° C. for 3~4 hours. Filter the suspension. Rinse with 150 g of n-heptane and dry the filter cake under reduced pressure at 65~75° C. for 10-16 hrs. obtain title compound (129.6 g, 96.5% purity in 82% yield; LC-MS (MS+=371.8); $^1$H NMR (CDCl$_3$, 400 MHz): δ=8.932 (s, 1H), 7.86 (m, 1H), 5.707 (s, 1H), 3.192-3.180 (d, 3H), 2.754 (s, 3H).

PREPARATION 12

N,7-Dimethylpyrido[2,3-d]pyrimidin-2-amine

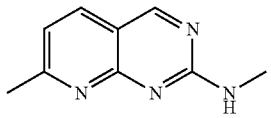

Treat a solution of 4-amino-2-(methylthio)pyrimidine-5-carbaldehyde (10 g, 59.1 mmol) in acetone (100 mL) with KOH (3.32 g, 59.1 mmol), stir at RT for 10 min, then concentrate to dryness. Treat the residue with EtOAc, wash with saturated. aqueous NaHCO$_3$, then brine, dry over Na$_2$SO$_4$ and concentrate to obtain 7-methyl-2-(methylthio)pyrido[2,3-d]pyrimidine. MS (m/z): 192.1 (M+1). Add a solution of methylamine in ethanol (33%, 80 mL) and heat at 110° C. overnight in a pressure tube. Remove the solvent under reduced pressure and purify the crude product by silica gel chromatography (50-100% EtOAc/Hexanes) to obtain the title compound (6.73 g, 65%, over two steps). MS (m/z): 175.1 (M+1).

PREPARATION 13

6-Bromo-N,7-dimethylpyrido[2,3-d]pyrimidin-2-amine

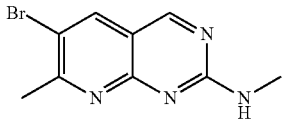

Cool a solution of N,7-dimethylpyrido[2,3-d]pyrimidin-2-amine (6.73 g, 38.6 mmol) in acetonitrile (160 mL) in an ice bath and shield from light with aluminum foil. Add N-bromosuccinimide (6.88 g, 38.6 mmol) and stir at 0° C. for 2 h. Transfer the reaction to a 5° C. refrigerator for 4 days. Collect the solid by filtration. Wash the solid with DCM and concentrate the washings to obtain the title compound (3.0 g, 31% yield). MS (m/z): 253.0/255.0 (M+1).

EXAMPLE 1

1-(3,3-Dimethylbutyl)-3-(2-fluoro-4-methyl-5-(7-methyl-2-(methylamino)pyrido[2,3-d]pyrimidin-6-yl)phenyl)urea

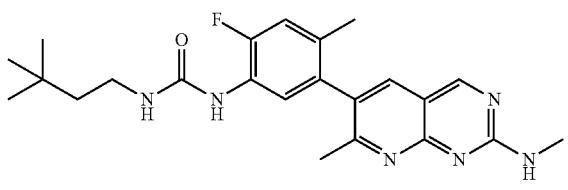 [SMILES: CNc1ncc2cc(-c3cc(NC(=O)NCCC(C)(C)C)c(F)cc3C)c(C)nc2n1]

Example 1 can be prepared with Method A, Method B, or Method C.

Method A:

Combine 1-(3,3-dimethylbutyl)-3-(2-fluoro-4-methyl-5-(4,4,5,5-tetramethyl-1,3,2-dioxaborolan-2-yl)phenyl)urea (25.9 g, 68.5 mmol), 7-methyl-2-(methylamino)pyrido[2,3-d]pyrimidin-6-yl trifluoromethanesulfonate (22.09 g, 68.5 mmol), and $NaHCO_3$ (17.28 g, 206 mmol) in 1,4-dioxane (500 mL) and water (125 mL) and sparge with argon for 20 minutes. Add tetrakis(triphenylphosphine)palladium (3.96 g, 3.43 mmol) and then heat under argon at 50° C. Add additional portion of 7-methyl-2-(methylamino)pyrido[2,3-d]pyrimidin-6-yl trifluoromethanesulfonate (300 mg, 0.55 mmol) and continue heating at 50° C. overnight. Cool the mixture to RT, collect the solid by filtration, and wash with water then diethyl ether. Treat the solid with acetonitrile (50 mL) and heat the slurry at 80° C. for 30 minutes. Collect the solid by filtration, wash with acetonitrile and dry under vacuum at 80° C. to obtain a pale yellow solid. Treat the solid with MeOH (50 mL), and heat the mixture at 80° C. for 1 hour. Cool to RT, collect the solid via filtration, wash with MeOH (20 mL), and dry under vacuum to obtain the title compound (22.5 g, 77% yield) as a pale yellow solid. MS (m/z): 425.2 (M+1).

Method B:

Sparge a suspension of 1-(3,3-dimethylbutyl)-3-(2-fluoro-4-methyl-5-(4,4,5,5-tetramethyl-1,3,2-dioxaborolan-2-yl)phenyl)urea (4.48 g, 11.8 mmol), 6-bromo-N,7-dimethylpyrido[2,3-d]pyrimidin-2-amine (3.0 g, 11.8 mmol) and $K_2CO_3$ (4.91 g, 35.6 mmol) in dioxane (80 mL) and water (20 mL) with argon, treat with tetrakis(triphenylphosphine)palladium (0.685 g, 0.593 mmol) and heat at 85° C. overnight. Remove the dioxane under reduced pressure, treat the mixture with EtOAc and brine, separate the layers, dry the organics over $Na_2SO_4$, concentrate and purify by silica gel chromatography (40% to 100% EtOAc/hexane, 100% EtOAc, 5% MeOH/EtOAc). Treat the material with $CH_3CN$, heat at 80° C. for 1 hour, cool to RT and collect the solid via filtration to afford the title compound (3.52 g, 70% yield) as a pale yellow solid. MS (m/z): 425.2 (M+1).

Method C:

Bubble with $N_2$ the mixture solvents 1,4-dioxane (1250 g) and water (200 g) in a reaction vessel. Heat the mixture to 80~85° C. Charge 100 g (0.31 mol, 1.0 eq. limited reagent) of 7-methyl-2-(methylamino)pyrido[2,3-d]pyrimidin-6-yl trifluoromethanesulfonate, 117.4 g (0.31 mol, 1.0 eq.) of 1-(3,3-dimethylbutyl)-3-(2-fluoro-4-methyl-5-(4,4,5,5-tetramethyl-1,3,2-dioxaborolan-2-yl)phenyl)urea, 128.7 g (0.93 mol, 3.0 eq.) of $K_2CO_3$ and 6.81 g (0.0093 mol, 0.03 eq.) of $Pd(dppf)Cl_2$ under nitrogen. Stir the mixture at 80~90° C. for 4~6 hours. Cool the mixture to 40~50° C. Concentrate and add 2000 g of water drop-wise below 30° C. After addition, stir the mixture at 10~30° C. for 6~8 hours. Filter and rinse with 200 g of water, then wash the cake. Dry the filter cake under reduced pressure at 60~70° C. for 14-16 hrs. to obtain Tech Grade API of title compound (158 g, 90.4% pure, assay: 63.4%, KF: 5%-6%). Dissolve the Tech Grade API of title compound in 1000 mL of DCM and 1000 mL of EtOH at 10~30° C. Add 50 g of Silica gel, 80 g of $Na_2S_2O_3.5H_2O$ and 10 g of active carbon. Heat the mixture to 40~50° C. and stir for 3~5 hours and cool to 10~30° C. Filter and wash the cake with 200 g of DCM/EtOH (1:1). Stir with 5 g of SilicaThiol at 40~50° C. and filter. Solvent exchange with 390.0 g of EtOH twice. Concentrate and filter the suspension, then wash the cake with 39.0 g of EtOH. Dry the filter cake under reduced pressure at 65~75° C. for 14-16 hrs to obtain API of title compound (61 g, 98.5% pure, assay: 97.5%, 65% yield; $^1H$ NMR (d6-DMSO, 400 MHz): δ=9.077 (s, 1H), 8.278 (s, 1H), 7.968-7.947 (d, 1H), 7.893 (s, 1H), 7.680 (s, 1H), δ 7.193-7.162 (d, 1H), 6.512-6.485 (m, 1H), 3.088-3.035 (m, 2H), 2.924-2.914 (d, 3H), 2.296 (s, 3H), 1.955 (s, 3H), 1.344-1.304 (m, 2H), 0.875 (s, 9H).

X-Ray Powder Diffraction

The XRD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction pattern, collected at ambient temperature and relative humidity, is adjusted based on NIST 675 standard peaks at 8.853 and 26.774 degrees 2-theta.

Free Base Crystalline Solid

Thus, a prepared sample of the free base crystalline solid of Example 1 is characterized by an XRD pattern using CuKa radiation as having diffraction peaks (2-theta values) as described in Table 1 below, and in particular having peaks at 16.0 in combination with one or more of the peaks selected from the group consisting of 6.9, 7.0, 18.2, and 23.2; with a tolerance for the diffraction angles of 0.2 degrees.

TABLE 1

X-ray powder diffraction peaks of the free base crystalline solid of Example 1:

| Peak | Angle (2-Theta °) | Intensity % |
| --- | --- | --- |
| 1 | 6.9 | 80.4 |
| 2 | 7.0 | 71.3 |
| 3 | 12.1 | 13.2 |
| 4 | 13.9 | 11 |
| 5 | 14.1 | 10.2 |
| 6 | 14.9 | 36.1 |
| 7 | 16.0 | 100 |
| 8 | 17.0 | 16.2 |
| 9 | 18.2 | 67.5 |
| 10 | 18.4 | 57.9 |
| 11 | 18.6 | 57.8 |
| 12 | 20.0 | 31.1 |
| 13 | 20.5 | 55.3 |
| 14 | 21.9 | 36.3 |

TABLE 1-continued

X-ray powder diffraction peaks of the free
base crystalline solid of Example 1:

| Peak | Angle (2-Theta °) | Intensity % |
|---|---|---|
| 15 | 22.1 | 38.3 |
| 16 | 23.2 | 59.6 |
| 17 | 23.7 | 46.8 |
| 18 | 26.0 | 20.7 |
| 19 | 28.0 | 20.2 |
| 20 | 29.1 | 32.2 |
| 21 | 29.6 | 16.5 |

It is generally known that bioavailability of a poorly soluble compound may be enhanced by formulating it as a solid dispersion in a polymer matrix. Such solid dispersions are dispersions of drug in an inert carrier matrix prepared by melting (fusion) of drug-polymer mixtures followed by solidification of the homogeneous molten mixture by rapid cooling (for example using processes such as hot melt extrusion), or by dissolving the drug and polymer in appropriate organic solvent followed by either solvent removal by evaporation (for example spray-drying) or by precipitation using antisolvent. Solid dispersions typically render the drug in an amorphous form which results in faster dissolution rate and/or higher degree (extent) and duration of supersaturation leading to enhanced oral bioavailability of poorly soluble compounds relative to the undispersed crystalline drug. Polymers that have been successfully used for solid dispersions include (but are not limited to) polyvinyl pyrrolidone (PVP), polyvinyl pyrrolidone-vinyl acetate (PVP-VA), hydroxypropyl methylcellulose (HPMC), hydroxypropyl methylcellulose acetate succinate (HPMCAS), hydroxypropyl methylcellulose phthalate (HPMCP-55), cellulose acetate phthalate (CAP), and Eudragit® EPO.

Physical and chemical stability of a solid dispersion are factors in the suitability of such formulations. Drug loading is another variable that can impact physical stability of the metastable amorphous form of drug as well as its in vivo performance. A preferred way to administer a solid dispersion in humans is by further formulating it as a capsule, a tablet, or other solid oral dosage form by adding a pharmaceutically acceptable carrier, and optionally other excipients, suitable for such dosage form manufacturing and performance. Solid Dispersions may be dosed by filling the powder or granulated blend into capsules, as a suspension in suitable vehicle, or any other suitable oral pharmaceutical dosage form such as (but not limited to) tablets, sachets, granules, sprinkles, etc.

Due to low bioavailability of Example 1, resulting from its poor solubility, an enabling formulation to achieve target exposures in dog and rat small animal studies and for clinical testing is desired. A neutral polymer PVP-VA (Kollidon® VA 64) resulted in solid dispersions that were both chemically and physically stable under accelerated stability testing (40° C.; relative humidity 75% over one month period, as well as upon long term storage (11 months for 20% drug load and 10 months for 40% drug load) under ambient conditions.

COMPOSITION EXAMPLE 1

20% Solid Dispersion Containing Example
1:PVP-VA (20:80)

Crystalline Example 1 is used for preparation of a solid dispersion. Polyvinyl pyrrolidone vinyl acetate (PVP-VA) is commercially available under brand name of Kollidon® VA 64 from BASF Corporation. Solvent is 1:1 Dichloromethane and Methanol, prepared by mixing equal volumes of dichloromethane (Fisher Scientific) and methanol (OmniSolv). sodium lauryl sulfate (Fisher Scientific) is commercially available.

Procedure:

A solid dispersion is prepared and spray-dried in two sub-batches. For the first sub-batch, Example 1 (22.22 g) is added to a 2000 mL bottle. 1180 mL of solvent (dichloromethane:methanol, 1:1) is added and the sample bath sonicated for about 20 minutes until all compound is dissolved resulting is a theoretical concentration of 19 mg/mL. To this solution, 88.86 g of PVP-VA is added and dissolved by mixing until a homogeneous solution is obtained. The solution of Example 1 and PVP-VA (20:80) in dichloromethane:methanol (1:1) is spray dried using a mini-spray-dryer (Buchi Mini Spray Dryer 290). The solution flow rate is 9-12 ml/min, with inlet temperature set at 100° C.-110° C. resulting in an outlet temperature of 37-55° C. For the second sub-batch, Example 1 (34.62 g) is added to a 2000 mL bottle. 1820 mL of solvent (Dichloromethane:Methanol, 1:1) is added and the sample bath sonicated for about 20 minutes until all compound is dissolved resulting in a theoretical concentration of 19 mg/mL. To this solution, 138.48 g of PVP-VA is added and dissolved by mixing until a homogeneous solution is obtained. The solution of Example 1 and PVP-VA (20:80) in dichloromethane:methanol (1:1) is spray dried using a mini-spray-dryer (Buchi Mini Spray Dryer 290). The solution flow rate is 14-15 ml/min, with inlet temperature set at 100° C.-110° C. resulting in an outlet temperature of 62-70° C. Spray-dried material collected from both sub-batches is mixed and dried further in a vacuum oven overnight between 40-60° C., and then stored under vacuum for another day at room temperature.

To 236.28 g of solid-dispersion containing Example 1:PVP-VA (20:80), 4.278 g of sodium lauryl sulfate is added and blended thoroughly in a large crystallization dish using a spatula to give a final composition containing 98% solid dispersion plus 2% sodium lauryl sulfate.

This formulation may be dosed by filling the blended powder into capsules, or as a suspension by suspending in a vehicle of, for example, 1% Hydroxyethylcellulose/0.25% polysorbate 80/0.05% Dow Corning antifoam 1510-US.

COMPOSITION EXAMPLE 2

40% Solid Dispersion Containing Example
1:PVP-VA (40:60)

Crystalline Example 1, polyvinyl pyrrolidone vinyl acetate (PVP-VA), solvent, and sodium lauryl sulfate are as described for Composition Example 1.

Procedure:

A solid dispersion is prepared by a spray-drying process substantially as described for Composition Example 1 using 3.79 g of Example 1, an appropriate volume of solvent (dichloromethane:methanol, 1:1) to obtain a 20 mg/mL concentrated solution. To this solution, 5.68 g of PVP-VA is added and dissolved by mixing until a homogeneous solution is obtained. The solution is spray dried substantially as described for Composition Example 1. The solution flow rate is set at 40% using 2 mm silicone tubing, with inlet temperature set at 80° C. resulting in outlet temperature of 34° C. Spray-dried material is collected and dried further in vacuum oven for 14 hours at room temperature, with a slow nitrogen feed and in the presence of desiccant.

To 6.64 g of solid-dispersion containing Example 1:PVP-VA (40:60), 0.0665 g of sodium lauryl sulfate is added and blended thoroughly in a jar using a spatula, resulting in a final composition containing solid dispersion and sodium lauryl sulfate in a ratio of 99:1.

This formulation may be dosed by filling the blended powder into capsules, or as a suspension by suspending in a vehicle of, for example, 1% Hydroxyethylcellulose/0.25% polysorbate 80/0.05% Dow Corning antifoam 1510-US.

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenvironments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site: http://cgap.nci.nih.gov). The database includes chromosomal aberrations for at least some of the malignancies of the present invention. The Wellcome Trust Sanger Institute Cancer Genome Project maintains a detailed online "Cancer Gene Census" of all human genes that have been causally linked to tumorigenesis (see http://www.sanger.ac.uk/genetics/CGP/Census) as well as the COSMIC (Catalogue of Somatic Mutations in Cancer) database of somatic mutations in human cancer (see http://www.sanger.ac.uk/genetics/CGP/cosmic). A further source containing abundant information on cytogenetic changes causally linked to various cancers is the Atlas of Genetics and Cytogenetics in Oncology and Haematology (http://atlasgeneticsoncology.org//Anomalies/Anomliste.html#MDS). These databases also include chromosomal aberrations for at least some of the malignancies of the present invention.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

The Ras/Raf/MEK/MAPK signaling pathway relays extracellular stimuli to the nucleus, thereby regulating diverse cellular responses including cell proliferation, differentiation and apoptosis. Perturbation of these processes by aberrant MAPK signaling such as genetic alterations often leads to malignant transformation. The importance of this signaling pathway in neoplasms is evident through the discovery of many mutant alleles that activate this pathway in a variety of human malignancies. Oncogenic mutations in receptor tyrosine kinases (RTKs), such as EGFR and cMet, or overexpression of RTKs and their ligands abnormally activate Ras and its downstream components. Activating Ras mutations have been detected in approximately 30% of human cancers. These mutations markedly diminish GTPase activity, thereby rendering Ras in the GTP-bound and active state. In mammals, the Ras family consists of three genes: K-Ras, N-Ras and H-Ras. K-Ras is often mutated in epithelial cancers, such as pancreatic, lung and colorectal cancer, while N-Ras mutations often occur in melanoma, liver and myeloid (AML, CML) malignancies. Activating mutations of B-Raf, a member of Raf family, have been discovered with high frequency in melanoma and thyroid carcinoma and, to a lesser extent, in colorectal, ovarian and lung cancer. Somatic mutations of MEK1 and MEK2 have been identified in melanoma patients. Finally, loss of negative regulators, such as members of the Sprouty family and GAPs (GTPase-activating proteins) such as NF1, can indirectly activate this pathway. It is believed that many tumors exhibit deregulation of Ras/Raf/MEK/MAPK pathway, making it an attractive target for therapeutic intervention.

The Raf proteins are composed of three members, A-Raf, B-Raf and C-Raf (also called Raf1), that play a pivotal role in transducing signals from Ras to downstream components MEK1/2 and ERK1/ERK2. Raf protein kinases have been shown to play a role in tumorigenesis including tumor cell proliferation, survival, invasion and angiogenesis, Sebolt-Leopold et al, *Nat Rev Cancer*, 2004, 4: 937-947; Wellbrock et al, *Nat Rev Mol Cell Biol*, 2004, 5: 875-885. MAPK pathway activation in tumor cells by multiple mechanisms such as mutations or overexpression of RTKs and Ras mutations, all go through Raf proteins. More importantly, activating mutations of B-RAF, Davies et al, *Nature*, 2002, 417: 949-954, are often observed in several malignancies including melanoma, colorectal, lung, ovarian and thyroid carcinomas. Almost 90% of the B-Raf mutations are a T1799A change in exon 15 which results is a Val to Glu amino acid substitution (B-Raf V600E). This mutation in B-Raf leads to constitutive kinase activity approximately 500 fold greater than that of wild type protein, and malignant transformation. Additional mutations, such as T529I, a threonine to isoleucine B-Raf gatekeeper mutation and G468A, a B-Raf secondary mutation at G1403C in exon 11 are also known and believed to play a role in causing, maintaining, or exacerbating malignant transformation, Whittaker et al, *Sci. Transl. Med.*, 2010, 2(35) ra41; Wan et al, *Cell*, 2004, 116: 855-867.

Recently, a B-Raf specific kinase inhibitor vemurafenib (also called PLX-4032) was approved by the United States Food and Drug Administration (FDA) for treatment of melanoma patients with B-Raf V600E mutation. Vemurafenib is efficacious and provides survival benefit in these patients. However, patients responsive to this drug generally develop drug resistance which leads to disease relapse in an average of 7 months. Similar to many other targeted therapies, the acquired resistance to B-RAF inhibition presents a therapeutic challenge to long-term survival benefit in this patient population.

To improve the benefit of B-Raf inhibitors, research continues to identify the mechanisms which render mutant B-RAF expressing melanoma cells resistant to vemurafenib. Recent studies have indicated that reactivation of the MAPK pathway is a mechanism of resistance to B-RAF inhibition. Resistant mechanisms primarily involve reactivation of ERK signaling through bypass mechanisms that are either Ras/RAF dependent, such as N-Ras activation, Nazarian et al, *Nature.* 2010, 468: 973-7, H-Ras activation (Su et al, *New England Journal of Medicine.* 2012, 366: 207-215) or C-RAF upregulation, (Johannessen et al, *Nature.* 2010, 468: 968-72; Montagut et al, *Cancer Res.* 2008, 68: 4853-61), aberrantly spliced variants of B-RAF V600E (Poulikakos et al, *Nature.* 2011, 480: 387-390, or Ras/RAF independent (Tpl2/COT overexpression) Johannessen et al, *Nature.* 2010, 468: 968-72. Consequently, multiple mechanisms could attenuate the effect of B-RAF inhibition on MAPK signaling in B-RAF mutant cancers. Although a gatekeeper mutation of B-RAF (T529I) that could cause resistance to BRAF inhibition has not yet been clinically identified, such a mutation has been experimentally demonstrated to cause resistance, Whittaker et al, *Sci Transl Med.* 2010, 2(35): ra41. Recent studies have also suggested that activation of MAPK-redundant signaling pathways by RTKs such as IGF-1R or PDGFRβ could play a role in acquired resistance to B-RAF inhibition; Nazarian et al, *Nature.* 2010, 468: 973-7; Villanueva et al, *Cancer Cell.* 2010, 18: 683-95; Shi et al, *Cancer Res.* 2011, 71: 5067-74. It is clear that MAPK reactivation is involved in many of these resistance mechanisms. A pan Raf inhibitor is expected to block MAPK reactivation.

Additionally, B-Raf specific inhibitors including vemurafenib and its close analogue N-[3-(5-chloro-1H-pyrrolo[2,3-b]pyridine-3-carbonyl)-2,4-difluorophenyl]propane-1-sulfonamide (PLX4720; a commercially available selective B-Raf inhibitor) were demonstrated to induce paradoxical pathway activation through dimerization with other Raf isoforms in a B-Raf wild type background, Hatzivassiliou G, et al. *Nature,* 2010, 464: 431-435; Poulikakos et al, *Nature,* 2010, 464: 427-430; Heidorn, et al, *Cell,* 2010, 140: 209-221. Vemurafenib is believed to activate the Raf/MEK/ERK pathway through binding B-Raf wild type and stimulating B-Raf-C-Raf dimerization. This paradoxical pathway activation by B-Raf specific inhibition is believed to be a major reason of skin side effects (such as squamous cell carcinoma) in some melanoma patients treated with vemurafenib. Vemurafenib is not approved for treatment of cancer patients with B-Raf wild type genetic background due to its paradoxical pathway activation activity in this genetic background.

The tested exemplified compound is a Raf kinase inhibitor inhibiting all isoforms of Raf proteins including A-Raf, B-Raf, C-Raf, and B-Raf V600E mutation. Due to its pan Raf activities, the tested exemplified compound is active against tumor cells with MAPK pathway activation by upstream signaling such as N-Ras mutation and K-Ras mutation, both with B-Raf wild type genetic background. Therefore, the tested exemplified compound has the potential for treating cancer patients with B-Raf mutation (such as melanoma, colorectal, lung, ovarian and thyroid carcinoma), N-Ras mutation, B-Raf wild type (such as melanoma, AML, CML, ALL, CLL, liver cancer), (Schubbert et al, *Nature Reviews Cancer,* 2007, 7: 295; Pylayeva-Gupta et al, *Nature Reviews Cancer,* 2011, 11: 761); or K-Ras mutation, B-Raf wild type (such as biliary tract, cervical, colorectal, endometrial, lung, ovarian, pancreatic, and liver; Schubbert et al, *Nature Reviews Cancer,* 2007, 7: 295; Pylayeva-Gupta et al, *Nature Reviews Cancer,* 2011, 11: 761) or other mechanism of Raf activation including upstream activating RTK mutation/overexpression. The tested exemplified compound is also active against melanoma tumor cells which developed resistance to vemurafenib. Therefore, it is believed that the tested exemplified compound will be effective for melanoma patients who have failed vemurafenib or other B-Raf inhibitors.

The tested exemplified compound is also an inhibitor of c-Kit. C-Kit is a receptor tyrosine kinase that normally controls the function of primitive hematopoietic cells, melanocytes and germ cells. Following binding with its ligand stem cell factor (SCF), c-Kit undergoes dimerization/oligomerization and autophosphorylation. Genetic mutations (such as L576P, K642E, T670I, and V654A) of c-Kit that constitutively activate c-Kit can lead to melanoma, acute myelogenous leukemia, and gastrointestinal stromal tumors (GIST), therefore, the tested exemplified compound has the potential to treat melanoma, acute myelogenous leukemia and GIST patients, Lennartsson et al, *Current Cancer Drug Targets,* 2006, 6: 65.

The exemplified compound can be used as a single agent or in combination with one or more other approved drugs for treatment of cancer patients. These cancer patients include: melanoma patients with B-Raf V600E mutation, melanoma patients who failed vemurafenib or other B-Raf inhibitors, melanoma patients with N-Ras mutation B-Raf wild type, melanoma patients with c-Kit overexpression or cKit mutation; colorectal cancer patients with B-Raf V600E mutation or K-Ras mutation B-Raf wild type; ovarian cancer patients with B-Raf V600E mutation or K-Ras mutation B-Raf wild type; lung cancer patients with B-Raf V600E mutation or K-Ras mutation B-Raf wild type; myeloid leukemia patients with N-Ras mutation B-Raf wild type, or c-Kit overexpression or c-Kit mutation; liver cancer patients with N-Ras or K-Ras mutation B-Raf wild type; pancreatic cancer patients with K-Ras mutation B-Raf wild type; thyroid carcinoma patients with B-Raf V600E or N-Ras mutation B-Raf wild type; biliary tract cancer patients with K-Ras mutation B-Raf wild type; GIST patients with c-Kit mutation or overexpression.

The following in vitro and in vivo studies demonstrate the Ras/Raf/MEK/ERK pathway signaling inhibitory activity of the exemplified compound. These assays are generally recognized by those skilled in the art as indicative of human clinical chemotherapeutic activity. Assays evidencing pan Raf inhibition and pathway signaling inhibitory activity may be carried out substantially as follows or by similar assays affording similar data. Unless otherwise stated, reported $IC_{50}$ values are absolute.

Enzymatic Assays of Kinase Activities of B-Raf, C-Raf and B-Raf Mutations

The test compound is evaluated for its inhibitory activities against human wild type B-Raf, human wild type C-Raf, human B-Raf V600E, human B-Raf V600E+T529I or human B-Raf V600E+G468A. T529I is a threonine to isoleucine B-Raf gatekeeper mutation and G468A is a B-Raf secondary mutation at G1403C in exon 11. The enzymatic assays of B-Raf, C-Raf and B-Raf mutations evaluate a property of Raf and MEK1 complex, which in the presence of ATP, catalyzes an enhanced ATP hydrolysis (Rominger, et al, *Arch. Biochem. Biophys.* 2007, 464: 130-137; US Patent Publication No. 2006/0211073). The ADP formed is monitored by the well-known coupled PK/LDH (pyruvate kinase/lactate dehydrogenase) system in the form of NADH oxidation, which can be monitored and detected spectrophotometrically by absorbance at 340 nm (A340; for principal of the method see Schindler et al, *Science,* 2000, 289: 1938-1942). Raf activated MEK1 ATPase activity is a property shared by all forms of Raf proteins.

Expression and Purification of Raf Proteins

Generally, cell lines are generated using commercially available materials by procedures known to and routinely used by those skilled in the art. The nucleotide sequences encoding full-length B-Raf wild type DNA (National Center for Biotechnology Information (NCBI), Reference Sequence NC_000007.13), C-Raf (National Center for Biotechnology Information (NCBI), Reference Sequence NC_000003.11) and A-Raf (National Center for Biotechnology Information (NCBI), Reference Sequence NC_000023.10) are known. See also, e.g., for B-Raf: S. Ikawa, et al., "B-raf, a new member of the raf family, is activated by DNA rearrangement," *Mol Cell Biol*, 8(6):2651-4 (1988); for C-Raf: M. Fukui, et al., "Molecular cloning and characterization of an activated human c-raf-1 gene," *Mol Cell Biol*, 7(5):1776-81 (1987); Bonner, et al., "The complete coding sequence of the human raf oncogene and the corresponding structure of the c-raf-1 gene," *Nucleic Acids Res.*, 14 (2), 1009-1015 (1986); for MEK1: C. F. Zheng, et al., "Cloning and characterization of two distinct human extracellular signal-regulated kinase activator kinases, MEK1 and MEK2," *J. Biol. Chem.*, 268 (15), 11435-11439 (1993); for tag information: J. Tsai, et al., "Discovery of a selective inhibitor of oncogenic B-Raf kinase with potent antimelanoma activity," *Proc. Natl. Acad. Sci. U.S.A.*, 105(8), 3041-3046 (2008); G. Hatzivassiliou, et al., "RAF inhibitors prime wild-type RAF to activate the MAPK pathway and enhance growth," *Nature*, 464 (7287), 431-435 (2010).

B-RafV600E (residues 433-726 containing V600E mutation) containing an N-terminal purification tag is expressed and purified essentially as described previously (Wan et al, *Cell*, 2004, 116, 855-867).

B-Raf V600E constructs containing a secondary T529I mutation or G468A mutation are generated by site directed mutagenesis (Quikchange, Strategene) of the base bRaf (433-726, V600E) construct.

Sequences that are used herein include: B-RafV600E (residues 433-726 containing V600E mutation) without N-terminal purification tag; B-RafV600E (residues 433-726 containing V600E and T529I mutations) without N-terminal purification tag; B-RafV600E (residues 433-726 containing V600E and G468A mutations) without N-terminal purification tag; BRAF-V600E; BRAF-V600E+T529I; BRAF-V600E+G468A; BRAF-wild type, full length; C-RAF; MEK1 protein sequence used for screening.

Enzymatic Assays Measuring Raf Kinase Activity

The test compound is evaluated for its inhibitory activities against wild type B-Raf, wild type C-Raf, B-Raf V600E, B-Raf V600E+T529I and B-Raf V600E+G468A. T529I is a B-Raf gatekeeper mutation and G468A is a B-Raf secondary mutation. The enzymatic assays of B-Raf, C-Raf and B-Raf mutations evaluate a property of Raf and MEK1 complex, which in the presence of ATP, catalyzes an enhanced ATP hydrolysis (Rominger, et al, *Arch. Biochem. Biophys.* 2007, 464: 130-137). The ADP formed is monitored by the well-known coupled PK/LDH (pyruvate kinase/lactate dehydrogenase) system in the form of NADH oxidation, which can be monitored and detected by absorbance at 340 nm (A340; for principal of the method see Schindler et al, *Science*, 2000, 289: 1938-1942). Raf activated MEK1 ATPase activity is a property shared by all forms of Raf proteins. In the B-Raf wild type enzymatic assay, the reaction mixture contains 1.2 nM B-Raf, 30 nM MEK1, 1000 uM ATP, 3.5 units (per 100 ul) of PK, 5 units (per 100 ul) of LDH, 1 mM phosphoenol pyruvate (PEP), and 280 uM of NADH. In the C-Raf assay, the reaction mixture contains 0.6 nM C-Raf, 26 nM MEK1, 2000 uM ATP, and the same amount of PK, LDH, PEP and NADH as above. In the B-Raf V600E assay, the reaction mixture contains 1.6 uM B-RafV600E, 26 nM MEK1, 200 uM ATP and the same amount of PK, LDH, PEP and NADH as above. In the B-RafV600E+T529I assay, the reaction mixture contains 6.2 nM B-RafV600E+T529I, 30 nM MEK1, 200 uM ATP and the same amount of PK, LDH, PEP and NADH as above. In the B-Raf V600E+G468A assay, the reaction mixture contains 3.5 nM B-Raf, 30 nM MEK1, 200 uM ATP and the same amount of PK, LDH, PEP and NADH as above. All assays are started by mixing the above mixture with test compound and monitoring at A340 continuously for approximately 5 hr. Reaction data at the 3 to 4 hour time frame are collected to calculate IC50 values.

For Example 1, the enzyme $IC_{50}$ result for B-Raf V600E is 6 nM and for C-Raf is 15 nM. These data evidence that the exemplified compound inhibits B-Raf V600E and C-Raf in these assays.

Example 1 is evaluated in further enzymatic assays carried out by substantially similar methods to those described above. Example 1 inhibits wild type B-Raf, B-Raf V600E+T529I and B-Raf V600E+G468A with $IC_{50}$ values of 9.8, 15.47 and 16.9 nM, respectively. These data evidence that Example 1 is a B-Raf inhibitor in these assays.

Enzymatic Assay of c-Kit Kinase Activity c-Kit is an important oncogene, and its overexpression and genetic mutations often occur in melanoma and gastrointestinal stromal tumor (GIST) patients. In the c-Kit enzymatic assay, the phosphorylation of poly E4Y by ATP catalyzed by human c-Kit is monitored spectrophotometrically. The ADP produced from the kinase reaction is coupled to pyruvate kinase/lactate dehydrogenase (PK/LDH) reactions where NAD is formed from pyruvate and NADH. NADH can be detected by absorbance at 340 nm, as described above for enzymatic assays of kinase activities of B-Raf, C-Raf and B-Raf mutations.

Expression and Purification of c-Kit Wild Type Receptor

Generally, cell lines are generated using commercially available materials by procedures known to and routinely used by those skilled in the art.

The nucleotide sequence encoding full-length human wild type c-Kit receptor DNA (National Center for Biotechnology Information (NCBI) Reference Sequence NC_000004.11), is known. See also, e.g., for human cKit protein sequence: Y. Yarden, Y., et al., "Human proto-oncogene c-kit: a new cell surface receptor tyrosine kinase for an unidentified ligand," *EMBO J.* 6 (11), 3341-3351 (1987); for GST fusion proteins: D. B. Smith, et al., "Single-step purification of polypeptides expressed in *Escherichia coli* as fusions with glutathione S-transferase," *Gene* 67 (1988) 31-40; D. B. Smith, "Purification of glutathione S-transferase fusion proteins," *Methods Mol. Cell. Biol.* 4 (1993) 220-229.

c-Kit Assays

The assay reaction mixture includes 6 nM human wild type c-KIT, 1 mg/mL Poly (Glu,Tyr) (Sigma), 1 mM Phosphoenol-pyruvate, 280 µM NADH, 5 U/3.5 U (per 100 ul) Pyruvate Kinase/Lactate Dehydrogenase, 85 mM Tris, pH 7.5, 17 mM $MgCl_2$, 0.0042% Triton® X-100, 0.005% BSA, 1% DMSO. Test compound is incubated with the reaction mixture for 0.5 hour before adding 200 µM ATP to start the reaction at 30° C. Reaction rates at 0.5 to 1 h are used to calculate % inhibition and $IC_{50}$'s.

A sequence that is used herein includes c-KIT with N-terminal GST fusion.

For Example 1, the human c-Kit inhibition $IC_{50}$ result is 21 nM. This data evidences the tested exemplified compound is a human wild type c-Kit inhibitor in this assay.

To further evaluate the test compound, it is tested against c-Kit mutations commonly occurring in melanoma and/or GIST. Ba/F3 cell line (from ATCC) are transfected with wild type (WT) c-Kit, c-Kit L576P (Willmore-Payne et al, *Human Pathology*, 2005, 36(5), 486; Willmore-Payne et al, *Human Pathology*, 2006, 37, 520), c-Kit K642E (Willmore et al, *Am J Clin Pathol*, 2004, 122(2), 206; Monsel et al, *Oncogene*, 2010, 29, 227), c-Kit T670I (Tamborini et al, *Oncogene*, 2006, 25, 6140), or c-Kit V654A (Tamborini et al, *Oncogene*, 2006, 25, 6140), respectively are established by retroviral transfection methods well known and used by those skilled in the art. The mutations are generated by polymerase chain reaction (PCR) mutagenesis and confirmed by automated sequencing of the PCR-amplified c-Kit expression construct. Ba/F3 stable cell lines are generated by transfecting with plasmid DNA. Expression of the appropriate c-Kit mutants is confirmed by Western blot analysis.

Wild type Ba/F3 cells are generally dependent on IL-3 for growth. After c-Kit transfection, these cells are grown in Ba/F3 ATCC recommended growth medium in the presence of stem cell factor (SCF), the ligand of c-Kit. The anti-proliferation activities of test compounds against these cells are tested in the presence of IL-3 or SCF.

DMSO to 500 µL of lysate in duplicate for final concentrations of 1 µM, 0.1 µM, 0.01 µM, and 0.001 µM. 5 µL of DMSO is added to 500 µL of lysate in quadruplicate for controls. After 15 minute incubation, desthiobiotin-ATP acylphosphate probe is added to each sample to a final concentration of 5 µM and incubated with the samples for 10 minutes. Following the probe reaction, samples are prepared for targeted mass spectrum analysis using ActivX standard protocol. Briefly, samples are prepared for trypsin digestion (denature, reduce alkylate), digested with trypsin, and desthio-biotinylated peptides are enriched on streptavidin resin.

Data Collection:

Enriched peptide samples are analyzed by LC-MS/MS on a Thermo-LTQ Velos ion trap mass spectrometer using ActivX data collection methodology for A375 V600E cells.

Data Analysis:

All quantitation is performed by extracting characteristic fragment ion signals from targeted MS/MS spectra and comparing signals in control and treated samples. ActivX software is used with manual validation/visual inspection performed as needed based on data flagging/filtering measures. All inhibition data points are visually verified, as are all data points showing variability outside of normal limits. Significance of data points showing >35% inhibition is determined according to the following formula: |average control peak areas−average treated peak areas|/(2*StdDev(Control peak areas)+|treated replicate one peak area−treated replicate two peak area|>0.8. $IC_{50}$ values are determined using IGOR® software.

TABLE 2

Anti-proliferation activities of Example 1 in Ba/F3 c-Kit cell lines
Anti-proliferation activities ($IC_{50}$, uM) of Example 1 in Ba/F3 c-Kit cell lines

| Test compound | Treatment | Ba/F3 | Ba/F3 c-Kit WT | Ba/F3 c-Kit L576P | Ba/F3 c-Kit K642E | Ba/F3 c-Kit T670I | Ba/F3 c-Kit V654A |
|---|---|---|---|---|---|---|---|
| Example 1 | SCF | ND | 0.062 | 0.179 | 0.047 | 0.29 | 0.086 |
| | IL-3 | ND | 2.858 | 2.079 | 1.200 | 5.919 | 2.942 |

The data in Table 2 evidences that Example 1 has cell proliferation and viability inhibitory activity against wild type c-Kit and the identified c-Kit genetic mutations in Ba/F3 cells.

Measurement of Raf Kinase Activities with Native Whole Enzymes Using KiNativ Assay of ActivX Biosciences Inc.

To further evaluate the enzymatic pan Raf activities of the test compound, it is evaluated in a KiNativ assay developed and carried out by ActivX Biosciences Inc. using whole cell lysates of A375 cells. A375 cells are human melanoma cells with a B-Raf V600E mutation, A-Raf wild type and C-Raf wild type.

Sample Preparation:

A375 (B-Raf V600E) cells from ATCC are lysed by sonication in commercially available lysis buffer, cell debris removed by centrifugation, and the resulting supernatant gel filtered into a commercially available kinase reaction buffer containing 20 mM $MnCl_2$. Final protein concentration of lysates are 10 mg/mL. 5 µL of each test compound is added from 100 µM, 10 µM, 1 µM, or 0.1 µM stock solutions in

TABLE 3

Pan Raf activities of Example 1 in ActivX KiNativ A375 whole cell lysate assay

| | % inhibition | | | | |
|---|---|---|---|---|---|
| Example 1 (nM) | 1000 | 100 | 10 | 1 | $IC_{50}$ (nM) |
| B-Raf (V600E) | 96.5 | 82.9 | 19.7 | 8.1 | 31 |
| B-Raf (V600E) | >98 | 82 | 7.5 | −10 | 47 |
| A-Raf (WT) | 72 | 53.6 | 13.4 | 4.3 | 44 |
| C-Raf (WT) | 79.3 | 50.8 | 23.9 | −11 | 42 |

As shown in Table 3, Example 1 inhibited A-Raf, B-Raf V600E and C-Raf with $IC_{50}$ values of 44, 31-47, and 42 nM, respectively. These data evidence Example 1's inhibition of A-Raf, C-Raf and B-Raf V600E in a whole cell lysate assay.

Example 1 Inhibits Cellular Phospho-ERK Activity

To investigate if the in vitro biochemical activities of Example 1 translate into cellular activities, Example 1 is used to treat melanoma cells, A375 V600E, and WM-266-4 V600E, A375 V600E-PLX4032 resistant cells (A375-res; generation described below) and HCT-116 (K-Ras mutant B-Raf wild type) cells, a colon tumor cell with a K-Ras mutation. A375 V600E, WM-266-4 V600E, HCT-116 K-Ras mutant B-Raf wild type are from ATCC. The cellular activities are assessed by an ELISA assay commercially available from TGR Biosciences to measure the phospho-ERK levels of each cell type.

A375 V600E, A375 V600E-PLX4032 resistant cells, WM-266-4 V600E, or HCT-116 (K-Ras mutant B-Raf wild type) cells are grown in growth medium (described below for CellTiterGlo Assay) in 96 well plates from PerkinElmer overnight, then are treated with Example 1 at 0 and 11 different serial dilution concentrations ranging from 0.17 to 10000 nM for 1 hour. The cells in each well are then lysed with 50 µl lysis buffer from TGR Biosciences. The phospho-ERK activities are determined with SureFire phospho-ERK AlphaScreen assay kit from TGR Biosciences per manufacturer's instruction.

Example 1 inhibited phospho-ERK level in a dose dependent manner in all cell lines tested. The $IC_{50}$ values for A375 V600E, WM-266-4 V600E, A375 V600E-res and HCT-116 (K-Ras mutant B-Raf wild type) cells are 3, 4.9, 9.7 and 132.8 nM, respectively. These data evidence that Example 1 inhibits downstream signaling in A375 V600E, WM-266-4 V600E, A375 V600E-res and HCT-116 K-Ras mutant B-Raf wild type cells as a result of Raf inhibition in this assay.

CellTiter-Blue Cell Proliferation and Viability Assay
A375 Cell Proliferation Assay A375 cells (catalog #CRL-1619) are obtained from the American Type Culture Collection (ATCC, Manassas, Va.). Briefly, cells are grown in DMEM High Glucose supplemented with 10% characterized fetal bovine serum (Invitrogen, Carlsbad, Calif.) and 1% Penicillin/Streptomycin/L-Glutamine at 37 degrees Celsius, 5% $CO_2$, and 95% humidity. Cells are allowed to expand until reaching 70-95% confluency at which point they are subcultured or harvested for assay use. A serial dilution of test compound is dispensed into a 384-well black clear bottom plate in triplicate. Six hundred twenty-five cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

Colo-205 Cell Proliferation Assay

Colo205 cells (catalog #HB-8307) are obtained from the American Type Culture Collection (ATCC, Manassas, Va.). Briefly, cells are grown in RPMI 1640 supplemented with 10% characterized fetal bovine serum (Invitrogen, Carlsbad, Calif.), 1 mM sodium pyruvate, and 1% Penicillin/Streptomycin/L-Glutamine at 37 degrees Celsius, 5% $CO_2$, and 95% humidity. Cells are allowed to expand until reaching 30-60% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

HT-29 Cell Proliferation Assay

HT-29 cells (catalog #HTB-38) are obtained from the American Type Culture Collection (ATCC, Manassas, Va.). Briefly, cells are grown in McCoy's 5A supplemented with 10% characterized fetal bovine serum (Invitrogen, Carlsbad, Calif.), and 1% Penicillin/Streptomycin/L-Glutamine at 37 degrees Celsius, 5% $CO_2$, and 95% humidity. Cells are allowed to expand until reaching 75-90% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

HCT-116 Cell Proliferation Assay

HCT-116 cells (catalog #CCL-247) are obtained from the American Type Culture Collection (ATCC, Manassas, Va.). Briefly, cells are grown in McCoy's 5A supplemented with 10% characterized fetal bovine serum (Invitrogen, Carlsbad, Calif.), and 1% Penicillin/Streptomycin/L-Glutamine at 37 degrees Celsius, 5% $CO_2$, and 95% humidity. Cells are allowed to expand until reaching 75-90% confluency at which point they are subcultured or harvested for assay use. A serial dilution of test compound is dispensed into a 384-well black clear bottom plate in triplicate. Six hundred twenty-five cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

SK-Mel-2 Cell Proliferation Assay

Sk-Mel-2 cells (catalog #HTB-68) are obtained from the American Type Culture Collection (ATCC, Manassas, Va.). Briefly, cells are grown in MEM supplemented with 10% characterized fetal bovine serum (Invitrogen, Carlsbad, Calif.), 1 mM sodium pyruvate, 0.1 mM non-essential amino acids, and 1% Penicillin/Streptomycin/L-Glutamine at 37 degrees Celsius, 5% $CO_2$, and 95% humidity. Cells are allowed to expand until reaching 70-95% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm.

Data is analyzed using Prism software (Graphpad, San Diego, Calif.) to calculate $IC_{50}$ values.

The A375, HT-29, and Colo-205 cells (ATCC) harbor a V600E mutation. The HCT-116 cells (ATCC) harbor a K-Ras mutation B-Raf wild type, and the SK-Mel-2 cells (ATCC) harbor an N-Ras mutation B-Raf wild type.

TABLE 4

Cell Proliferation and Viability Inhibition

Cell Proliferation Inhibition $IC_{50}$, nM

| Example No. | A375 | HT-29 | Colo-205 | HCT-116 | SK-Mel-2 |
|---|---|---|---|---|---|
| 1 | 9 | 7 | 27 | 224 | 158 |

The data in Table 4 evidences the exemplified compound inhibits proliferation and viability of the specified cells harboring the identified mutations in this assay.

Proliferation and Viability Inhibition Activity

Example 1 is tested for proliferation and viability inhibition activity across a diverse panel of human tumor cell lines in CellTiter-Glo assays.

Generally, for the CellTiter-Glo assay (Promega), cells are cultured in Dulbecco's modified Eagle's medium (DMEM, Thermo Scientific) supplemented with 10% fetal bovine serum (FBS, Invitrogen). Cells ($5 \times 10^3$) maintained in growth medium, are plated onto poly-D-Lysine-coated well in 96 well plates (BD Biosciences) a day before the treatment. The cells are treated for 48-72 hours, and then analyzed for proliferation and viability using the CellTiter-Glo Luminescent Cell Viability Assay according to manufacturer's instructions (Promega) and a SpectraMax plate reader (Molecular Devices). Nonlinear regression and sigmoidal dose-response curves are used to calculate the half maximal inhibitory concentration ($IC_{50}$) with GraphPad Prism 4 software.

Additional N-RAS mutant B-Raf wild type hematologic cancer cell lines were tested for sensitivity to Example 1. N-Ras activating mutations are common in hematologic cancers occurring at a frequency of 10-30%. Two B-Raf V600E mutant melanoma cell lines (A-375 and SK-Mel-28), nine N-Ras mutant hematologic cell lines (HL-60, THP-1, TALL-1, C8166, H9, IM-9, GA-10 clone 4, P31-FUJ, MOLT-4) and seven N-Ras wild-type cell lines (LOUCY, HEL, U266, EB2, P30-OHK, NOMO-1, CCRF-CEM) were tested, and the $IC_{50}$ data reported. While there was a range of sensitivity among these cell lines, 7 of the 9 hematologic cancer cell lines with N-Ras mutations B-Raf wild type were sensitive to submicromolar concentrations of Example 1 ($IC_{50} < 1$ μM).

TABLE 5

Example 1 Proliferation and Viability Inhibition Activity in nM

| Abs IC50 | Rel IC50 | CELL_LINE_Designation | Commercially Available |
|---|---|---|---|
| 0.04 | 0.03 | SK-Mel-28 | ATCC |
| 0.05 | 0.04 | COLO-829 | ATCC |
| 0.06 | 0.03 | HepG2 | ATCC |
| 0.08 | 0.03 | THP-1 | ATCC |
| 0.11 | 0.03 | A375 | ATCC |
| 0.13 | 0.06 | SK-Mel-5 | ATCC |
| 0.17 | 0.09 | NCI-H1993 | ATCC |
| 0.19 | 0.12 | LOVO | ATCC |
| 0.2 | 0.25 | GA-10-Clone-4 | ATCC |
| 0.2 | 0.14 | HL-60 | ATCC |
| 0.24 | 0.22 | Calu-6 | ATCC |
| 0.33 | 0.19 | H9 | ATCC |
| 0.33 | 0.33 | KATOIII | ATCC |
| 0.38 | | IM-9 | ATCC |
| 0.39 | 0.23 | BxPC-3 | ATCC |
| 0.44 | 0.13 | HuH-7 | JCRB Cellbank |
| 0.44 | | P31-FUJ | JCRB Cellbank |
| 0.6 | 0.42 | DMS-53 | ATCC |
| 0.68 | 0.21 | NUGC-3 | Health Science Research Resources Bank |
| 0.69 | 0.23 | SW900 | ATCC |
| 0.72 | 0.42 | HCT-116 | ATCC |
| 0.75 | | TALL-1 | JCRB Cellbank |
| 0.8 | 0.36 | Hep3B2.1-7 | ATCC |
| 0.81 | 0.2 | A2780 | Sigma-Aldrich |
| 0.83 | 0.41 | NCI-H2030 | ATCC |
| 0.91 | 0.14 | NCI-H1299 | ATCC |
| 0.93 | 0.69 | NCI-H1975 | ATCC |
| 0.98 | 0.76 | Hs746T | ATCC |
| 0.98 | 0.5 | HT-1080 | ATCC |
| 0.98 | 1.87 | MV-4-11 | ATCC |
| 1.09 | 0.56 | C8166 | Sigma-Aldrich |
| 1.09 | 0.31 | MIA-PaCa-2 | ATCC |
| 1.1 | | U-266 | ATCC |
| 1.14 | 0.34 | AGS | ATCC |
| 1.22 | 0.38 | AsPC-1 | ATCC |
| 1.22 | 1.08 | LN 229 | ATCC |
| 1.27 | 0.33 | NCI-H2052 | ATCC |
| 1.43 | | P30-OHK | JCRB Cellbank |
| 1.5 | | CCRF-CEM | ATCC |
| 1.87 | 2.01 | SNU-449 | ATCC |
| 1.96 | 0.19 | 22RV1 | ATCC |
| 1.96 | 0.31 | SK-HEP-1 | ATCC |
| 1.99 | 0.59 | huH-1 | JCRB Cellbank |
| 2.63 | | NOMO-1 | JCRB Cellbank |
| 2.86 | 0.46 | SW620 | ATCC |
| 2.91 | 2.03 | Caki-1 | ATCC |
| 4.42 | 2.07 | A549 | ATCC |
| 4.5 | 0.22 | NCI-H522 | ATCC |
| 4.92 | 0.26 | RKO | ATCC |
| 5.18 | 0.66 | DU-145 | ATCC |
| 5.21 | 0.76 | U-118-MG | ATCC |
| 5.72 | 0.87 | MKN45 | JCRB Cellbank |
| 6.27 | 0.69 | NCI-H23 | ATCC |
| 6.93 | | LOUCY | ATCC |
| 8.35 | 12.74 | NCI-H1436 | ATCC |
| 9.58 | 5.32 | CaOV-3 | ATCC |
| 11.63 | 10.89 | BT-474 | ATCC |
| 11.92 | 1.58 | NCI-H2009 | ATCC |
| 13.37 | 6.97 | NCI-H838 | ATCC |
| 15.07 | 16.27 | NCI-H1694 | ATCC |
| 15.09 | 1.01 | M059K | ATCC |
| 15.13 | 19.95 | NCI-H2170 | ATCC |
| >20 | 4.58 | 786-0 | ATCC |
| >20 | 0.6 | C3A | ATCC |
| >20 | 0.5 | EB2 | ATCC |
| >20 | >20 | HCC70 | ATCC |
| >20 | | HEL | ATCC |
| >20 | 0.06 | HT-29 | ATCC |
| >20 | >20 | LN 18 | ATCC |
| >20 | 2.74 | LNCaP-Clone-FGC | ATCC |
| >20 | 0.26 | MDA-MB-436 | ATCC |
| >20 | 1.21 | MOLT-4 | ATCC |
| >20 | 0.47 | NCI-H1155 | ATCC |
| >20 | 0.99 | NCI-H1573 | ATCC |
| >20 | 0.36 | NCI-H1793 | ATCC |
| >20 | >20 | NCI-H2081 | ATCC |
| >20 | >20 | NCI-H2126 | ATCC |
| >20 | 1.18 | NCI-H2228 | ATCC |
| >20 | 12.55 | NCI-H661 | ATCC |
| >20 | >20 | PC-3 | ATCC |
| >20 | 11.72 | PLC-PRF-5 | ATCC |
| >20 | >20 | SiHa | ATCC |
| >20 | 10.8 | SK-OV-3 | ATCC |
| >20 | 4.34 | U-87-MG | ATCC |

The data above evidences A375 melanoma cells are sensitive to Example 1. Among the most sensitive cell lines in this screen are HepG2 and THP-1 cells. HepG2 is derived from a hepatocelluar carcinoma, THP-1 is an AML cell line, and both carry activating N-RAS mutations B-Raf wild type. The data evidence the pan Raf inhibitory activity and intervention of upstream signaling activation by Example 1 in this assay.

Example 1 Inhibits Cell Growth of HCT-116 Cells with K-Ras Mutation:

K-Ras mutation B-Raf wild type is one of the most common and most important mutations in many cancer types, including pancreatic, lung and colorectal cancer (Bos, *Cancer Research*, 1989, 49(17): 4682). K-Ras mutation leads to the activation of Ras/Raf/MEK/MAPK cascade which contributes to the cell transformation and malignancy. To assess the anti-proliferation activity of Example 1 in K-Ras mutant B-Raf wild type cells, colon tumor HCT-116 cells (ATCC) harboring a K-Ras mutation B-Raf wild type are used in a CellTiter-Glo cell proliferation and viability assay. Example 1 inhibited HCT-116 K-Ras mutation B-Raf wild type proliferation and viability in a dose dependent manner with an $IC_{50}$ of 178 nM. These data evidence Raf inhibitory activity by Example 1 intervenes in inappropriate activated upstream signaling in this assay.

Example 1 Inhibits Cell Growth of Tumor Cells with N-Ras Mutation:

N-Ras is often mutated in melanoma, acute myeloid leukemia (AML), and liver cancer (Bos, *Cancer Research*, 1989, 49(17): 4682). N-Ras mutations B-Raf wild type leads to MAPK activation through Raf proteins, particularly C-Raf. Example 1's anti-proliferation activity in N-Ras mutant B-Raf wild type tumor cells, human melanoma cell line SK-MeI-2 harboring N-Ras mutation Q61R, and B-Raf wild type (ATCC), is tested in the CellTiterGlo assay for cell proliferation and viability inhibition and Western blot analysis is carried out.

Immunoblotting (Western Blot) Analysis

Testing is carried out at doses of 0, and 11 serial dilutions ranging from 0.17 to 10000 nM. Protein lysates are generated by treatment of the cells with RIPA lysis buffer from Millipore. Western blotting analysis is performed substantially as described in Yadav et al, *Molecular Carcinogenesis*, 2011, 50: 346-52. Briefly, SDS-PAGE is performed on cell lysates containing 20 ug of total protein using 4-20% Novex® triglycine gradient gels (Invitrogen). Protein is transferred onto 0.45 µM nitrocellulose membranes using NuPAGE® Transfer Buffer (Invitrogen) and 10% methanol at 100 V, 4° C. for 1 hr. Generally, the primary antibody is used at 1:1000 dilution, and secondary antibody at 1:20000 dilution. Proteins are detected using the Odyssey Infrared Imaging System (Li-COR Biosciences). Antibodies against ERK1/2, phospho-ERK1/2, phospho-MEK1/2, and actin are obtained from Cell Signaling Technology.

Example 1 exhibits dose dependent phospho-MEK and phospho-ERK inhibition in SK-MeI-2 cells harboring N-Ras mutation Q61R, and B-Raf wild type as determined by Western Blot analysis. Phospho-ERK activity is substantially eliminated at a dose of 370 nM.

Example 1 inhibits SK-MeI-2 cell proliferation and viability in the CellTiter-Glo assay with an $IC_{50}$ of 188 nM. These data evidence that Example 1 inhibited cell proliferation and viability in SK-MEL-2 cells harboring wild type B-Raf and N-Ras mutation Q61R in this assay.

Example 1 Activity in Inhibiting Vemurafenib-Resistant Melanoma Cells:

Vemurafenib (PLX4032) and PLX4720 are inhibitors of mutant B-Raf V600E (Johannessen et al, *Nature*, 2010, 468: 968-72; Montagut et al, *Cancer Res.* 2008, 68: 4853-61; Wagle et al, *Journal of Clinical Oncology*, 2011, 29: 3085-96). Some of the patients who initially respond to vemurafenib therapy develop drug resistance and become refractory within an average of 7 months, Whittaker et al, *Sci Transl Med.* 2010, 2: 35-41. A vemurafenib-resistant cell line is generated by chronic treatment of the human melanoma cell line A375 (ATCC) harboring the B-Raf V600E mutation with increasing concentrations PLX4720.

Generation of B-RAF V600E Melanoma Cell Lines Resistant to B-RAF Inhibition

To generate resistant cells, A375 B-Raf V600E cells (ATCC) are cultured in growth medium, as described above for the CellTiter-Glo assay, in the presence of gradually increasing concentrations of N-[3-(5-chloro-1H-pyrrolo[2,3-b]pyridine-3-carbonyl)-2,4-difluorophenyl]propane-1-sulfonamide (PLX4720; a commercially available selective B-Raf inhibitor) from 0.02 to 2 µM through approximately 4 months and 30 passages to afford a resistant cell line designated as A375res. The resistance of A375res to vemurafenib and PLX4720 is confirmed by MAPK reactivation by Western blot analysis and shift of $IC_{50}$ values in CellTiter-Glo cell proliferation and viability assay.

In these A375res cells, PLX4032 loses much of its activity shifting nearly 30 fold from 252 nM to greater than 7 µM. Example 1 activity against these resistant cells evidences an $IC_{50}$ of 34 nM shifting only 3 fold from 11 nM. These data evidence that Example 1 inhibited cell proliferation and viability in A375res cells in this assay.

Example 1 has Minimal Paradoxical Pathway Activation:

Recent published studies (see above) suggest that B-Raf specific inhibitors, such as vemurafenib (PLX-4032) induce "paradoxical pathway activation" through B-Raf dimerization with other Raf isoforms in B-Raf wild type backgrounds. Vemurafenib is not approved for treatment of melanoma cancer patients with B-Raf wild type genetic background. This paradoxical pathway activation is also believed to be a cause of skin side effects (such as squamous cell carcinoma) in some melanoma patients treated with vemurafenib.

Example 1 is tested against HCT-116 (ATCC) cells harboring a B-Raf wild type and K-Ras mutation in a CellTiter-Glo viability assay. Testing is carried out at doses of 0, and 11 serial dilutions ranging from 0.17 to 10000 nM. The phospho-MEK and phospho-ERK activities were evaluated by Immunoblotting (Western Blot) analysis.

Example 1 evidenced minimal paradoxical pathway activation, and maintains phospho-MEK and phospho-ERK inhibiting activities in HCT-116 cells harboring B-Raf wild type and K-Ras genetic background. Example 1 substantially eliminates phospho-ERK signal at doses above 41 nM in this assay. Since Example 1 also evidences C-Raf inhibition (prior assays, above) it is believed paradoxical pathway activation should not occur.

Example 1 Inhibits Cell Growth of Tumor Cells with B-Raf V600E Mutation:

B-Raf mutations, particularly B-Raf V600E in human cancer are often observed in human malignancies including melanoma, colorectal, lung, and ovarian cancers. This mutation in B-Raf may lead to constitutive kinase activity and malignant transformation. Example 1 is tested in the CellTiter-Glo assay in three melanoma cell lines A375 (ATCC), WM-266-4 (ATCC) and SK-Mel-28 (ATCC), and two colon tumor cell lines HT-29 (ATCC) and Colo-205 (ATCC); all five cell lines have a B-Raf V600E mutation.

TABLE 6

Example 1 activity against tumor cells harboring B-Raf V600E mutation

| Cell line | Mutation | Tumor type | IC$_{50}$ (nM) |
|---|---|---|---|
| A375 | B-Raf V600E | melanoma | 9.2 |
| WM-266-4 | B-Raf V600E | melanoma | 52.9 |
| SK-Mel-28 | B-Raf V600E | melanoma | 29 |
| HT-29 | B-Raf V600E | colon | 7.3 |
| Colo-205 | B-Raf V600E | colon | 27 |

Example 1 inhibited cell viability of three melanoma cell lines, A375, WM-266-4 and SK-Mel-28 with IC$_{50}$ values of 9.2, 52.9 and 29 nM, respectively. Similarly, Example 1 inhibited cell viability of two colon cell lines, HT-29 and Colo-205 with IC$_{50}$ values of 7.3 and 27 nM. The data evidences that Example 1 is active in inhibiting cell viability and growth of tumor cells with B-Raf V600E mutation in this assay.

Example 1 also inhibited phospho-MEK and phospho-ERK activities in the A375 cells tested above that were further evaluated by Western Blot analysis evidencing inhibition of downstream signaling in a dose dependent manner. Phospho-ERK activity was substantially eliminated at 41 nM.

In Vivo Activity

To evaluate in vivo activity of Example 1, A375 V600E (ATCC) and HCT-116 K-Ras mutant B-Raf wild type (ATCC) xenograft tumor models are used. Briefly, 10×10$^6$ cells (A375) or 5×10$^6$ cells (HCT-116) in a 1:1 medium and matrigel mix (0.2 mL total volume) are implanted by subcutaneous injection in the hind leg of nude female rats (NIH model No. NIHRNU-M from Taconic). A total of 8 rats in each group are used for the efficacy study, and a total of 3-4 rats in each group are used for a pharmacodynamic study. The Eli Lilly and Company Animal Care and Use Committee approved all the experimental protocols. Treatment is initiated with oral administration (gavage) of Example 1 or vehicle (20% Captisol®, 25 mM phosphate, pH 2.0) in 0.6 mL volume when tumor size reaches approximately 500 mg. Example 1 is orally dosed twice a day at 5, 10, 15, and 20 mg/kg for 21 days for A375 xenograft model, or 15 and 30 mg/kg for 21 days for HCT-116 xenograft model. Tumor growth and body weight are monitored over time to evaluate activity and signs of toxicity. Bidimensional measurements of tumors are performed twice a week and tumor volumes are calculated based on mid-axis length and mid-axis width. Tumor volume data are transformed to a log scale to equalize variance across time and treatment groups. The log volume data are analyzed with a two-way repeated measures analysis of variance by time and treatment using the MIXED® procedures in SAS® software (version 8.2). The correlation model for the repeated measures is spatial power. Treated groups are compared to the control group at each time point. The MIXED® procedure is also used separately for each treatment group to calculate adjusted means and standard errors at each time point. Both analyses account for the autocorrelation within each animal and the loss of data that occurs when animals with large tumors are removed from the study early. The adjusted means and standard errors are plotted for each treatment group versus time.

In the A375 xenograft models all dose groups evidenced tumor growth inhibition and tumor growth regression, and there was no animal body weight loss in any of these groups. In the HCT-116 xenograft model, the 30 mg/kg group showed statistically significant tumor growth inhibition. These data evidence in vivo activity by Example 1 and support the enzymatic, cell lysate and cell proliferation data correlates to in vivo activity.

In a separate study to assess the pharmacodynamic (PD) effects of Example 1 in the A375 xenograft model, a single dose study with doses ranging from 3.125 to 50 mg/kg is carried out.

Two hours post a single dose treatment, a dose dependent PD effects is observed as evidenced by Western Blot analysis. Phospho-MEK and phospho-ERK inhibition was observed in all dose groups and 25 mg/kg almost completely eliminated phospho-MEK and phospho-ERK activities in this model.

We claim:

1. A compound which is 1-(3,3-dimethylbutyl)-3-(2-fluoro-4-methyl-5-(7-methyl-2-(methylamino)pyrido[2,3-d]pyrimidin-6-yl)-phenyl)urea, or a pharmaceutically acceptable salt thereof.

2. The compound according to claim 1 which is 1-(3,3-dimethylbutyl)-3-(2-fluoro-4-methyl-5-(7-methyl-2-(methylamino)pyrido[2,3-d]pyrimidin-6-yl)phenyl)urea.

3. The compound according to claim 2 wherein the compound is in a crystalline form characterized by a X-ray powder diffraction pattern having characteristic peaks, in 2θ±0.2, occurring at 16.0 and one or more of 6.9, 7.0, 18.2, and 23.2.

4. A pharmaceutical composition comprising a compound which is 1-(3,3-dimethylbutyl)-3-(2-fluoro-4-methyl-5-(7-methyl-2-(methylamino)pyrido[2,3-d]pyrimidin-6-yl)-phenyl) urea, or a pharmaceutically acceptable salt thereof, in association with a pharmaceutically acceptable carrier.

5. A pharmaceutical composition comprising a compound which is 1-(3,3-dimethylbutyl)-3-(2-fluoro-4-methyl-5-(7-methyl-2-(methylamino)pyrido[2,3-d]pyrimidin-6-yl)-phenyl)urea, or a pharmaceutically acceptable salt thereof, and a pharmaceutically acceptable carrier, diluent, or excipient.

6. The pharmaceutical composition according to claim 5 comprising the compound which is 1-(3,3-dimethylbutyl)-3-(2-fluoro-4-methyl-5-(7-methyl-2-(methylamino)pyrido[2,3-d]pyrimidin-6-yl)-phenyl)urea.

7. The pharmaceutical composition according to claim 6 wherein the compound is in a crystalline form characterized by a X-ray powder diffraction pattern having characteristic peaks, in 2θ±0.2, occurring at 16.0 and one or more of 6.9, 7.0, 18.2, and 23.2.

8. A pharmaceutical composition comprising a compound which is 1-(3,3-dimethylbutyl)-3-(2-fluoro-4-methyl-5-(7-methyl-2-(methylamino)pyrido[2,3-d]pyrimidin-6-yl)phenyl)urea, or a pharmaceutically acceptable salt thereof, and polyvinyl pyrrolidone vinyl acetate (PVP-VA).

9. The pharmaceutical composition according to claim 8 comprising the compound which is 1-(3,3-dimethylbutyl)-3-(2-fluoro-4-methyl-5-(7-methyl-2-(methylamino)pyrido[2,3-d]pyrimidin-6-yl)-phenyl)urea.

10. The pharmaceutical composition according to claim 9 wherein the compound is in a crystalline form characterized by a X-ray powder diffraction pattern having characteristic peaks, in 2θ±0.2, occurring at 16.0 and one or more of 6.9, 7.0, 18.2, and 23.2.

11. The pharmaceutical composition according to claim 8 wherein the PVP-VA is Kollidon® VA 64.

12. The pharmaceutical composition according to claim 9 wherein the PVP-VA is Kollidon® VA 64.

13. The pharmaceutical composition according to claim 10 wherein the PVP-VA is Kollidon® VA 64.

14. A method of treating cancer, comprising administering to a patient in need thereof, an effective amount of a compound which is 1-(3,3-dimethylbutyl)-3-(2-fluoro-4-methyl-5-(7-methyl-2-(methylamino)pyrido[2,3-d]pyrimidin-6-yl)-phenyl)urea, or a pharmaceutically acceptable salt thereof, wherein the cancer is selected from the group consisting of thyroid cancer, ovarian cancer, melanoma, acute myelogenous leukemia (AML), and colorectal cancer.

15. The method according to claim 14 comprising the compound which is 1-(3,3-dimethylbutyl)-3-(2-fluoro-4-methyl-5-(7-methyl-2-(methylamino)pyrido[2,3-d]pyrimidin-6-yl)-phenyl)urea.

16. The method according to claim 15 wherein the compound is in a crystalline form characterized by a X-ray powder diffraction pattern having characteristic peaks, in 2θ±0.2, occurring at 16.0 and one or more of 6.9, 7.0, 18.2, and 23.2.

17. The method according to claim 14, wherein the cancer is melanoma.

18. The method according to claim 15, wherein the cancer is melanoma.

19. The method according to claim 16, wherein the cancer is melanoma.

20. The method according to claim 14, wherein the cancer is colorectal cancer.

21. The method according to claim 15, wherein the cancer is colorectal cancer.

22. The method according to claim 16, wherein the cancer is colorectal cancer.

* * * * *